US011584943B2

United States Patent
Soussan et al.

(10) Patent No.: US 11,584,943 B2
(45) Date of Patent: Feb. 21, 2023

(54) METHOD FOR CONVERTING CO₂ BY MEANS OF BIOLOGICAL REDUCTION

(71) Applicants: UNIVERSITE DE MONTPELLIER, Montpellier (FR); CENTRE NATIONAL DE LA RECHERCHE SCIENTIFIQUE, Paris (FR); ECOLE NATIONALE SUPERIEURE DE CHIMIE DE MONTPELLIER, Montpellier (FR)

(72) Inventors: Laurence Soussan, Montpellier (FR); Azariel Ruiz-Valencia, Lyons (FR); Djahida Benmeziane, Montpellier (FR); José Sanchez-Marcano, Sussargues (FR); Marie-Pierre Belleville, Saint Georges d'Orques (FR); Delphine Paolucci-Jeanjean, Saint Gely du Fesc (FR)

(73) Assignees: UNIVERSITÉ DE MONTPELLIER, Montpellier (FR); CENTRE NATIONAL DE LA RECHERCHE SCIENTIFIQUE, Paris (FR); ECOLE NATIONALE SUPERIEURE DE CHIMIE DE MONTPELLIER, Montpellier (FR)

( * ) Notice: Subject to any disclaimer, the term of this patent is extended or adjusted under 35 U.S.C. 154(b) by 113 days.

(21) Appl. No.: 15/734,280

(22) PCT Filed: Jun. 4, 2019

(86) PCT No.: PCT/FR2019/051316
§ 371 (c)(1),
(2) Date: Dec. 2, 2020

(87) PCT Pub. No.: WO2019/234344
PCT Pub. Date: Dec. 12, 2019

(65) Prior Publication Data
US 2021/0222212 A1  Jul. 22, 2021

(30) Foreign Application Priority Data
Jun. 5, 2018  (FR) ...................................... 1854867

(51) Int. Cl.
C12P 7/40 (2006.01)
C12N 1/20 (2006.01)
C12R 1/01 (2006.01)

(52) U.S. Cl.
CPC ................ *C12P 7/40* (2013.01); *C12N 1/205* (2021.05); *C12R 2001/01* (2021.05)

(58) Field of Classification Search
CPC ............. Y02C 20/40; C12P 7/40; C12P 5/023
See application file for complete search history.

(56) References Cited

FOREIGN PATENT DOCUMENTS

| EP | 2 944 696 A1 | 11/2015 | |
|---|---|---|---|
| EP | 3 301 181 A1 | 4/2018 | |
| WO | WO-2011089151 A2 * | 7/2011 | ............. C09K 8/665 |

OTHER PUBLICATIONS

Patil et al. "Genome Sequence of Type Strains of Genus *Stenotrophomonas*" Frontiers in Microbiology |Mar. 2016 | vol. 7 | Article 309, 6pgs (Year: 2016).*
Alfonso-Gordillo, G. et al. "*Stenotrophomonas maltophilia* isolated from gasoline-contaminated soil is capable of degrading methyl tert-butyl ether" *Electronic Journal of Biotechnology*, 2016, pp. 12-20, vol. 23.
Assih, E.A. et al. "*Stenotrophomonas acidaminiphila* sp. nov., a strictly aerobic bacterium isolated from an upflow anaerobic sludge blanket (UASB) reactor" *International Journal of Systematic and Evolutionary Microbiology*, 2002, pp. 559-568, vol. 52.
Fang, Z. et al. "Biodegradation of wool waste and keratinase production in scale-up fermenter with different strategies by *Stenotrophomonas maltophilia* BBE11-1" *Bioresource Technology*, 2013, pp. 286-291, vol. 140.
Li, H. et al. Supporting Online Material for "Integrated Electromicrobial Conversion of CO₂ to Higher Alcohols" *Science*, Mar. 16, 2012, pp. 1-12, vol. 335, No. 1596.
Mukherjee, P. et al. "Genomic Potential of *Stenotrophomonas maltophilia* in Bioremediation with an Assessment of Its Multifaceted Role in Our Environment" *Frontiers in Microbiology*, Jun. 2016, pp. 1-14, vol. 7, Article 967.
Soussan, L. et al. "Alkane biohydroxylation: Interests, constraints and future developments" *Journal of Biotechnology*, 2016, pp. 117-142, vol. 222.
Urszula, G. et al. "Isolation and Characterization of a Novel Strain of *Stenotrophomonas maltophilia* Possessing Various Dioxygenases for Monocyclic Hydrocarbon Degradation" *Brazilian Journal of Microbiology*, 2009, pp. 285-291, vol. 40, No. 2.

(Continued)

*Primary Examiner* — Thane Underdahl
(74) *Attorney, Agent, or Firm* — Saliwanchik, Lloyd & Eisenschenk

(57) ABSTRACT

The invention relates to a process for the recovery of CO₂ by biological reduction comprising a step of bringing a liquid phase containing the bacterium *Stenotrophomonas maltophilia* into contact with a CO₂-containing gas phase under conditions allowing the production of formate and/or methane from said CO₂. The process according to the invention can be implemented in particular in a closed reactor or a semi-closed reactor or a continuous reactor, electrochemically assisted or not.

20 Claims, 6 Drawing Sheets

(56) References Cited

OTHER PUBLICATIONS

Written Opinion in International Application No. PCT/FR2019/051316, dated Oct. 21, 2019, pp. 1-4.
Vieira, A. M. S. et al. "Microbial Populations of an Upflow Anaerobic Sludge Blanket Reactor Treating Wastewater from A Gelatin Industry" Environmental Technology, 2001, pp. 1477-1485, vol. 22.

* cited by examiner

METHOD FOR CONVERTING $CO_2$ BY MEANS OF BIOLOGICAL REDUCTION

CROSS-REFERENCE TO RELATED APPLICATION

This application is the U.S. national stage application of International Patent Application No. PCT/FR2019/051316, filed Jun. 4, 2019.

The invention relates to a microbiological process for the reduction of $CO_2$ to formate and/or methane, catalyzed by *Stenotrophomonas maltophilia*. According to the invention, this $CO_2$ reduction process can be intensified by the supply of exogenous electrons and protons. This supply can be achieved by the use of the bacteria in an electrolytic device (bioelectrolyzer). The process according to the invention can advantageously be used to treat $CO_2$-rich industrial or agricultural fumes or biogas containing chiefly a mixture of methane and $CO_2$, in order to reduce the $CO_2$ content of said fumes or biogas.

TECHNOLOGICAL BACKGROUND

Carbon dioxide ($CO_2$) accounts for more than 75% of global greenhouse gas (GHG) emissions, with annual anthropogenic emissions of roughly 25 to 35 Gt. These emissions come primarily from heavy industries and energy production, such as cement plants, aluminum and steel production sites, coal or fuel power plants, etc., as well as from road transport.

The use of $CO_2$ as an industrial raw material is currently being considered as one of the possible solutions for reducing atmospheric emissions of this gas.

In this context, the direct conversion of anthropogenic $CO_2$ to alternative fuels (such as methane, $C_1$-$C_5$ alcohols or formic acid) has become a major research topic over the last fifty years. However, the $CO_2$ molecule has a high chemical stability and $CO_2$ activation therefore requires relatively high temperatures and pressures as well as efficient and selective catalysts.

Homogeneous or heterogeneous catalysts have been developed, which catalyze hydrogenation, artificial photosynthesis or electrochemical reduction reactions to obtain fuels from $CO_2$. Nevertheless, these chemical conversion pathways still have low efficiency, durability and/or selectivity.

Biological processes for $CO_2$ activation have also been developed. These biological processes are particularly attractive because they consume little energy and they generally avoid reagents and/or by-products that could have a negative impact on the environment. To date, however, only processes using photosynthetic microorganisms, namely microalgae or cyanobacteria, have reached an industrial scale. The main products of $CO_2$ recovery by these processes are lipids or sugars that can then be transformed into biodiesel or biofuel. The open basin technology has enabled a change of scale in the recovery of $CO_2$ by microalgae. However, the development of this process still remains limited due to (i) the need for sunlight, which implies shallow photobioreactor depths (and therefore large surfaces), (ii) problems of nutrient mass transfer, (iii) a substantial need for water, (iv) the need to maintain a basic pH (8-10) and (v) the need to harvest the microorganisms to extract the compounds of interest therefrom. All of these constraints are reflected by low productivities and relatively high costs.

On a laboratory scale, cyanobacteria have been genetically modified to produce alcohols directly from $CO_2$. Very recently, the metabolic pathway of carbon assimilation of the cyanobacterium *Synechococcus elongatus* PCC 7942 has been directed toward the production of 2,3-butanediol from $CO_2$ and glucose in the dark. Such an advance overcomes limitations related to the need for sunlight. Nevertheless, the need to add glucose makes this bioprocess economically unattractive. Moreover, the biological stability of the modified cyanobacteria is still insufficient to allow its use on an industrial scale.

A pathway for the enzymatic synthesis of formate (basic form of formic acid) from carbon dioxide ($CO_2$) was also studied. More precisely, formate dehydrogenase (FDH) type enzymes extracted from microorganisms were purified and modified to improve their catalytic performance and used to reduce $CO_2$ to formate (Alissandratos et al. 2013, Appl Environ Microbiol., 79(2), 741-4; Spinner et al., 2012 Catal. Sci. Technol., 2, 19-28). Recently, nitrogenase type enzymes have also been reported as capable of catalyzing the reduction of $CO_2$ to formate, to carbon monoxide, to acetate or to methane, in addition to their nitrogen $N_2$ reduction activity (Khadka et al. 2016, Inorg. Chem., 55, 8321-8330; Zheng et al. 2018, Nature Microbiology, 3, 281-286). Nevertheless, the addition of an expensive cofactor is necessary to carry out the bioconversion reaction, making these alternatives incompatible with industrial application.

Electrochemically assisted reactors (also called bioelectrolyzers) inoculated with electroactive lithoautotrophic bacteria are another biological pathway for $CO_2$ conversion. Various products such as formate, acetate, $C_3$-$C_5$ alcohols, polyhydroxybutyrate (PHB) or biomass could be obtained. In these systems, two configurations have been implemented: (1) the electrons necessary for $CO_2$ reduction are supplied directly by the polarized cathode and the protons, in turn, come from the oxidation of water at the anode or (2) the electrons from the cathode are transported to the bacteria by electrochemical mediators (such as dihydrogen or formate) which can be added to the medium or generated in situ at the polarized cathode. However, up to now, the feasibility of configuration (1) has been demonstrated only in the case where an organic electron donor is also present in the medium, which reduces the economic attractiveness of this system. Furthermore, the use or in situ production of formate or of a clean and expensive energy carrier such as dihydrogen ($H_2$) remains problematic in configuration (2).

SUMMARY OF THE INVENTION

While working on $CO_2$ recovery, the inventors discovered that the bacterium *Stenotrophomonas maltophilia*, known for its ability to bind $CO_2$ through its carboxylase enzymes, is also able to reduce $CO_2$ to formate and/or methane. Methane is particularly attractive because it is a fuel whose combustion produces few air pollutants ($NO_x$ or $SO_x$ type) and releases less $CO_2$ per unit of energy (nearly 30% less) than the combustion of fossil fuels such as oil or coal. Methane is also a precursor to synthesis gases ($H_2$/CO/$CO_2$ mixtures) that are currently used in the industrial production of methanol, ammonia and hydrocarbons (Société Chimique de France, 2013). Formic acid, or methanoic acid, which is the acid form of formate, is in turn an aliphatic carboxylic acid of natural origin, which is in the form of a colorless liquid with a persistent odor. Formic acid has many applications in the leather and textile industries, in the composition of dyes and treatment products, insecticides, solvents, smokes, anti-mold treatment products, etc., but also in the perfume and agri-food industries as an aromatic molecule. Recently, it has been shown that formic acid can be used as fuel in fuel cells (Yu et al., 2008, Journal of Power Sources, 182(1), 124-132) or to store hydrogen which can then be released by dehydrogenation of formic acid (Fellay et al. 2008, Angewandte Chemie, 120(21), 4030-4032). The possibility of using formic acid as an energy carrier suggests that the need for formic acid will increase in the coming years. Moreover, formate can be used in secondary bioprocesses to obtain energy sources such as methane (Conrad, Contribution of hydrogen to methane production and control of hydrogen concentrations in methanogenic soils and sediments, FEMS Microbiology Ecology, 28(3) (1999) 193-202) or alcohols (Li et al., Integrated electromicrobial conversion of $CO_2$ to higher alcohols, Science, 335 (2012) 1596; Pen et al., An innovative membrane bioreactor for methane biohydroxylation. Bioresource Technology, 174 (2014) 42-52).

This new reduction pathway by S. maltophilia has a number of advantages compared with existing bioprocesses. Indeed, this biocatalyst is a native cell. In comparison with enzymes, it is therefore not necessary to carry out protein extractions or to add cofactors under stoichiometric conditions, as the cells already have their own stock. This cell also does not require genetic modifications, which are poorly tolerated on an industrial scale. Furthermore, no supply of dihydrogen ($H_2$) or photons (light) is required for the $CO_2$ reduction reaction because the cell has an intracellular stock of proton and electron donors, which it accumulates during the preculture phase (for example on acetate derived from methane oxidation or on a mixture of peptone and yeast extract).

An object of the invention is therefore a process for the recovery of $CO_2$ by biological reduction comprising a step of bringing a liquid phase containing the bacterium Stenotrophomonas maltophilia into contact with a $CO_2$-containing gas phase under conditions allowing the reduction of said $CO_2$, in particular to formate and/or methane.

In particular, the contact step can be carried out at 30° C., ±10° C., in particular at 30° C.±5° C., under atmospheric pressure or slight overpressure (up to 0.5 bar).

The liquid phase advantageously comprises mineral salts useful for the maintenance or survival of bacteria during the $CO_2$ reduction reaction. The person skilled in the art will know how to adapt the mineral salt composition. For example, the liquid phase contains water and phosphates and/or $MgCl_2$, etc.

Advantageously, the step of bringing the aqueous liquid phase into contact with $CO_2$ is carried out in a closed reactor, or in a semi-closed reactor.

Another object of the invention is the intensification of said biological $CO_2$ reduction process. Since the intracellular stock of proton and electron donors is limited, the inventors have demonstrated that it is possible to supply exogenous, or extracellular, protons and electrons, i.e. other than the intracellular protons and electrons of Stenotrophomonas maltophilia, so that the $CO_2$ reduction reaction is sustained over time. For example, it is possible to introduce into the reactor an electron and proton donor, such as a biopolymer and in particular polyhydroxybutyrate (PHB) and/or a bioelectrolysis type electrochemical assistance. Indeed, the inventors have shown that Stenotrophomonas maltophilia is capable of using the electrons from a weakly polarized cathode and the protons derived from the oxidation of water at the anode. In an embodiment, the energy supplied to the bioelectrolysis is of green origin, solar in particular, which makes this process energy self-sufficient.

Thus, another object of the invention is a process for intensifying $CO_2$ reduction by the bacterium Stenotrophomonas maltophilia comprising a step according to which exogenous PHB or electrochemical assistance (bioelectrolysis) is added to the reactor.

According to the invention, identified products of $CO_2$ reduction are formate and/or methane. It is also possible to couple the use of Stenotrophomonas maltophilia to another microorganism, in particular a microorganism capable of using the formate contained in the liquid to produce other molecules of interest, such as methane, lactate or alcohols, in particular $C_1$-$C_5$ alcohols (such as methanol, isobutanol or methyl-1-butanol).

Another object of the invention is the use of a Stenotrophomonas maltophilia bacterium for the production of formate and/or methane and/or more generally any product whose carbon oxidation number is lower than that of $CO_2$, by $CO_2$ reduction.

Another object of the invention is a process for the treatment of a biogas or industrial fumes rich in $CO_2$ or agricultural fumes rich in $CO_2$ comprising a step of $CO_2$ reduction by biological reduction comprising a step according to which said biogas or industrial fumes or agricultural fumes are brought into contact with a liquid phase containing the bacterium Stenotrophomonas maltophilia under conditions allowing $CO_2$ reduction.

Another object of the invention is a process for the production of formate from $CO_2$, comprising a step according to which a $CO_2$-containing gas phase is brought into contact with a liquid phase containing the bacterium Stenotrophomonas maltophilia under conditions allowing the reduction of the $CO_2$ to formate.

Another object of the invention is a process for the production of methane from $CO_2$, comprising a step according to which a $CO_2$-containing gas phase is brought into contact with a liquid phase containing the bacterium Stenotrophomonas maltophilia under conditions allowing the reduction of $CO_2$ to methane.

DETAILED DESCRIPTION OF THE INVENTION

Figure 1:
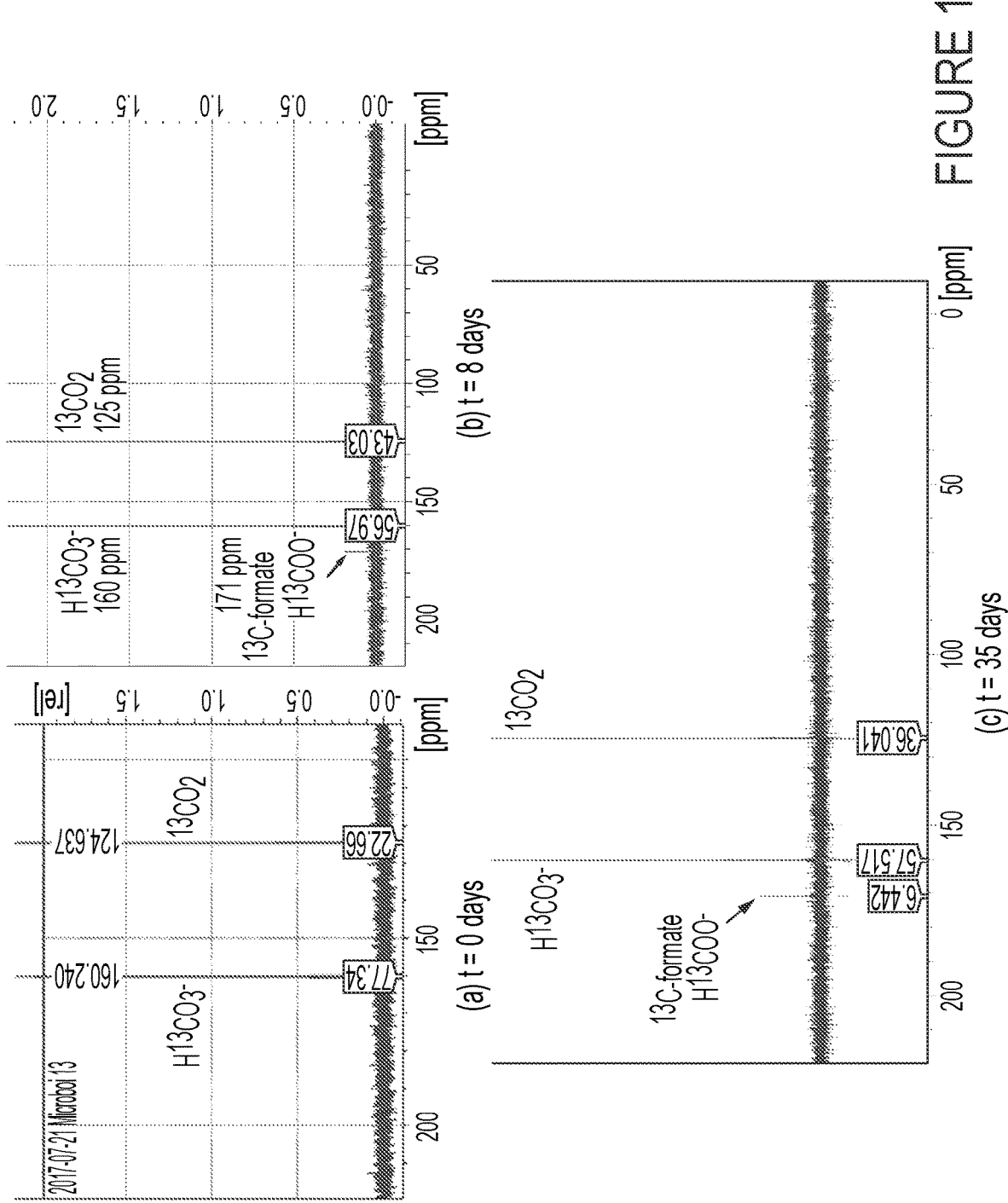
FIG. 1: NMR spectra of a suspension of Stenotrophomonas maltophilia used for $^{13}CO_2$ reduction tests in a closed reactor and under reference conditions: (a) at t=0 days, (b) at t=8 days and (c) at t=35 days.

The inventors discovered that *Stenotrophomonas maltophilia* is capable of producing formate and methane ($CH_4$) by direct reduction of $CO_2$ under mild operating conditions. In a particularly interesting manner, the inventors have shown that *Stenotrophomonas maltophilia* is able to produce formate and methane ($CH_4$) using $CO_2$ as the sole carbon source, without the need to supply cofactors, organic molecules, dihydrogen ($H_2$) or expensive growth factors.

In the context of the invention, $CO_2$ reduction is understood to mean any reaction allowing the carbon oxidation number of $CO_2$ to be reduced to a lower degree than in $CO_2$.

*Stenotrophomonas maltophilia* is a gram-negative aerobic bacterium of the family Pseudomonadaceae. To date, it has never been used for industrial purposes. However, the inventors have discovered that this bacterium is particularly attractive for the production of molecules of interest from $CO_2$. Indeed, the inventors discovered that this bacterium has the capacity to produce formate and/or methane from $CO_2$ as the sole carbon source, after having advantageously been first cultured in autotrophic conditions, i.e. in pure aerobic culture on a usual organic medium of the Lysogeny Broth Miller type, or in co-culture with a methanotrophic bacterium, such as *Methylosinus trichosporium* OB3b, on a mineral medium brought into contact with a methane/air mixture (1:1 v/v). The co-culture route is particularly advantageous because it guarantees an optimal carbon balance; indeed, methane, of renewable origin, is the sole source of carbon necessary for the culture.

Advantageously, the liquid phase comprises at least 3 $g_{dry\ cells}/L$ of the bacterium *Stenotrophomonas maltophilia*, at least 10 $g_{dry\ cells}/L$, at least 20 $g_{dry\ cells}/L$, 30 $g_{dry\ cells}/L$, 40 $g_{dry\ cells}/L$, 50 $g_{dry\ cells}/L$, 60 $g_{dry\ cells}/L$, 70 $g_{dry\ cells}/L$, 80 $g_{dry\ cells}/L$, 90 $g_{dry\ cells}/L$, 100 $g_{dry\ cells}/L$.

Advantageously, and whatever the culture mode, the cultures are carried out at 30° C., ±10° C. and at atmospheric pressure or slight overpressure (up to 0.5 bar).

According to the invention, the $CO_2$-containing gas phase brought into contact with the liquid reaction medium containing the bacterium *Stenotrophomonas maltophilia* can be atmospheric air. The gas phase may otherwise be pure $CO_2$ or a gas mixture, such as a mixture of $CO_2$-air, $CO_2$—$N_2$, $CO_2$—$O_2$, $CO_2$—$CH_4$, $CO_2$—$H_2$, $CO_2$—$N_2$—$H_2$, $CO_2$—$CH_4$—$H_2$, $CO_2$—$CH_4$-air, $CO_2$—$CH_4$—$N_2$ or $CO_2$—$CH_4$—$O_2$. In an embodiment, the gas phase contains or consists of biogas. In another embodiment, the gas phase contains or consists of $CO_2$-rich industrial or agricultural fumes. In a particular embodiment, the gas phase comprises at least 5%, 10%, 20%, 30%, 40%, 50%, 60%, 70%, 80%, 90% $CO_2$. Advantageously, the gas phase comprises at least 30% $CO_2$. It is also possible to use a gas phase comprising 100% $CO_2$. In an embodiment, the gas phase comprises between 30 and 100% $CO_2$.

In one reaction embodiment, the reaction medium contains 20 mM phosphate buffer at pH 7.0±0.1 and 5.0 mM $MgCl_2$. In another embodiment, the reaction medium contains 1.3 mM KCl, 28.0 mM $NH_4Cl$, 29.8 mM $NaHCO_3$ and 5.0 mM $NaH_2PO_4$. The skilled person can select the appropriate reaction medium for the reduction of $CO_2$ to formate by *Stenotrophomonas maltophilia*.

Since formate and/or methane and/or any other product whose carbon oxidation number is lower than that of $CO_2$ is obtained directly by $CO_2$ reduction, the yield of formate and/or methane and/or any other product whose carbon oxidation number is lower than that of $CO_2$ from the process according to the invention depends directly on the $CO_2$ supply. The skilled person will know how to adapt the $CO_2$ concentrations to the desired yields.

According to the invention, the $CO_2$ supply can be achieved by any known means and in particular by membrane contactors (Pen et al. 2014, Bioresource Technology, 174, 42-52), a porous gas distribution frit (Kim et al. 2010, Biotechnology and Bioprocess Engineering, 15(3), 476-480; Duan et al. Bioresource Technology, 102(15), 7349-7353) or a simple gas-liquid contact in a closed reactor (Pen et al. 2014, Bioresource Technology, 174, 42-52).

In an embodiment, the $CO_2$ recovery process is implemented in a closed (batch) reactor. Alternatively, the process can be implemented in a semi-closed (fed-batch) reactor.

According to the invention, the $CO_2$-containing gas phase can be injected into the headspace of the closed reactor. In an embodiment, it is possible to remove the air present in the headspace of the closed reactor prior to the injection of the gas phase, so as to place the reaction under an atmosphere consisting solely of the gas phase.

Alternatively or additionally, the gas phase can be injected in the center of the closed or semi-closed reactor, in the core of the liquid phase containing the bacterium *Stenotrophomonas maltophilia*, in particular by means of a gas distributor.

In the case of a semi-closed (fed-batch) reactor, the $CO_2$-containing gas phase is supplied continuously, preferentially by bubbling, into the reactor.

In one example embodiment, the pH in the reaction medium, i.e. the liquid phase, is maintained between 5 and 8, preferentially at pH 6.5, ±0.5. Advantageously, the $CO_2$ dissolved in the water forms a sufficient buffer to allow the pH to be maintained, without external regulation.

Similarly, the temperature in the reaction medium is preferentially maintained between 20° C. and 50° C., preferably between 25° C. and 35° C., and even more preferably at 30° C., ±1.

According to the invention, it is possible, prior to the reaction step, i.e. prior to bringing the bacterium into contact with $CO_2$ to produce formate and/or methane, to place the bacterium in a culture medium under temperature and pH conditions favorable to its growth.

"Culture medium" is understood to mean the medium in which bacteria are grown, to produce bacterial biomass. The culture medium conventionally comprises the chemical elements strictly necessary for bacterial growth in a form usable by the bacteria, i.e. a source of carbon, of mineral salts and of water. Standard media are available commercially, described in the scientific literature or in the catalogs of bacterial strain suppliers. The skilled person knows which are the minimum required components without which *Stenotrophomonas maltophilia* cannot grow and can cultivate such a bacterium without difficulty. The general culture conditions (temperature, composition of the medium, stirring, etc.) allowing the growth or the maintenance of *Stenotrophomonas maltophilia*, are easily defined by the skilled person.

This preliminary culture step can for example allow the bacterium to accumulate donors of protons and electrons necessary for the $CO_2$ reduction reaction to formate and/or methane according to equations (1) and (2) and/or (1) and (3):

$$CO_2 + H^+ + 2e^- \rightarrow HCOO^- \quad \text{(equation 1)}$$

$$CO_2 + 8H^+ + 8e^- \rightarrow CH_4 + 2H_2O \quad \text{(equation 2)}$$

$$HCOO^- + 7H^+ + 6e^- \rightarrow CH_4 + 2H_2O \quad \text{(equation 3)}$$

Alternatively or additionally, it is possible to add to the reactor an exogenous electron and proton donor, such as a biopolymer, so as to provide the bacteria with the electrons and protons necessary for the reaction, even in the absence or after exhaustion of intracellular donors. In particular, it is possible to add polyhydroxybutyrate (PHB) to the reactor. In an embodiment, the PHB is produced beforehand by methanotrophic bacteria from methane, in particular renewable methane (Pieja et al., Distribution and selection of poly-3-hydroxybutyrate production capacity in methanotrophic proteobacteria, *Microbial. Ecology*, 62(3) (2011) 564-573). Such an embodiment is particularly advantageous from an economic point of view.

In an embodiment, exogenous PHB is added to the reactor. Preferentially between 30 mg/L and 3 g/L exogenous PHB is added in the liquid phase, in particular about 0.3 g/L.

Figure 7:
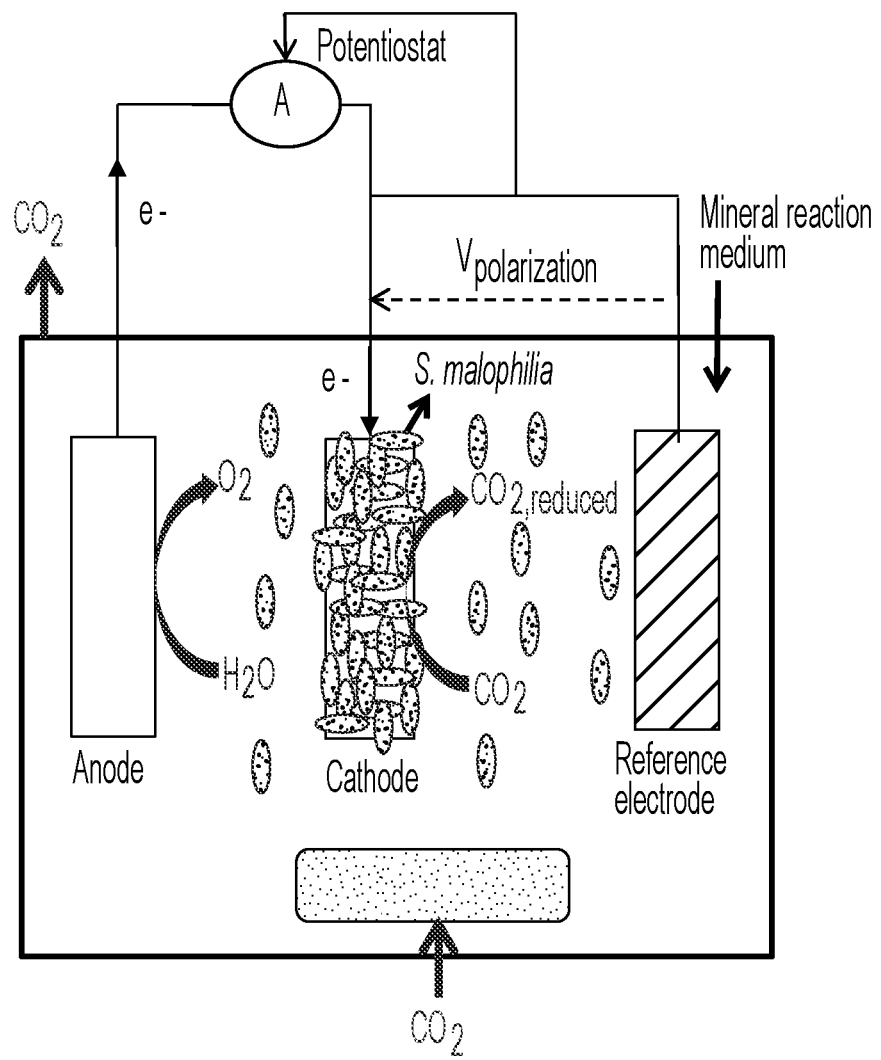
FIG. 7. Diagram and principle of an example embodiment of a semi-closed reactor, assisted by electrolysis (or bioelectrolyzer) for the $CO_2$ reduction reaction according to the process of the invention.

Alternatively or additionally, and in particular in the case of a semi-closed reactor, it can be particularly advantageous to use an electrochemical assistance device. Such a device, housed inside the reactor and in contact with the bacterium, can be used to supply electrons and protons to the bacterium. Electrochemical assistance can in particular be of the bioelectrolysis type (FIG. 7). Advantageously, the energy used to operate the bioelectrolyzer is solar energy.

Different materials can be used for the anode and the cathode, as long as they are electron conductive. For example, the cathode can be made of stainless steel, graphite or felt. The anode can be made of platinum, stainless steel, graphite or felt.

Advantageously, the ratio active cathode surface area/reactor volume is comprised between 1 and 100 $m^2/m^3$, preferentially about 10 $m^2/m^3$. "Active surface" is understood to mean the geometrical surface exposed to the anode. The ratio anode projected geometrical surface area/cathode projected geometrical surface area is preferentially comprised between 1 and 10, more preferentially roughly equal to 2. The polarization potential range can for example be from −1.5 V to 0 V vs Ag/AgCl, in particular −1 V to −0.5 V, for example −0.7 V or −0.8 V.

So as to optimize the $CO_2$ reduction reaction, it is possible to add ammonium and/or ammonia in the liquid phase and/or ammonia in the gas phase, in particular between 5 mmol/L and 100 mmol/L, preferentially between 20 and 30 mmol/L.

Alternatively or additionally, the liquid phase comprises, in addition to the bacterium *Stenotrophomonas maltophilia*, another microorganism capable of using the formate derived from $CO_2$ reduction to form more complex metabolites, such as methane, lactate or alcohols. The inventors have shown that such a consortium can lead to a synergy capable of intensifying the flow of $CO_2$ reduced by the bacterium *Stenotrophomonas maltophilia*.

All or part of the process according to the invention can be implemented on a laboratory scale or on an industrial scale, i.e. on fermenters, or reactors, of medium capacity (about 0.1 L to 100 L) or of large capacity (100 L to several hundred $m^3$).

Another object of the invention is the intensification of the $CO_2$ reduction process by the bacterium *Stenotrophomonas maltophilia* by means of an addition of exogenous PHB or an electrochemical assistance (bioelectrolysis) as described above.

In a particular embodiment, the $CO_2$ reduction reaction by the bacterium *Stenotrophomonas maltophilia* can be promoted by continuously removing the formate produced in the liquid phase of the reactor in the form of formate and/or formic acid. The skilled person knows the possible techniques to continuously remove the formate produced.

In another embodiment of the process according to the invention, the formate-enriched liquid and mineral reaction medium can be used as recovered in a secondary process or bioprocess aimed at converting the formate produced into molecules with higher added value. The skilled person knows the possible techniques for converting the formate produced.

In a particular embodiment, the formate production process according to the invention comprises the steps consisting in:

Introducing *Stenotrophomonas maltophilia* into a reactor containing a reaction medium; Supply the reaction medium, or liquid phase, with a $CO_2$-containing gas phase; and optionally Recovering the formate produced in the reactor by $CO_2$ reduction, in the form of formate and/or formic acid.

In another embodiment of the process according to the invention, the formate-enriched mineral reaction medium can be used as recovered in a secondary process aimed at converting the formate produced into molecules with higher added value.

In another embodiment of the process according to the invention, the formate produced is recovered in the form of formic acid from the reaction medium.

In a particular embodiment, the step of recovery of formic acid from the reaction medium is carried out by electrodialysis or by liquid-liquid extraction with a co-solvent. These recovery devices allow continuous recovery of formic acid and thus avoid the possible inhibition of bacteria by an excess of product, while obtaining a formic acid free of impurities (such as salts from the reaction medium).

In the case of continuous recovery of the product, a continuous supply of reaction medium can be made to the bioreactor. In the case of an electrodialysis recovery process, a bipolar electrodialysis module is advantageously coupled with a microfiltration module to continuously separate and recover the formate product in its acid form (formic acid). In particular, bipolar electrodialysis can be carried out on a reaction medium without biocatalysts, obtained continuously after separating the bacteria from the medium by a tangential microfiltration module. Bipolar electrodialysis consists in combining a bipolar membrane to acidify the formate to formic acid and monopolar membranes to extract the salts from the reaction medium.

The formate and/or formic acid obtained from such a microbiological process can be advantageously used in any industry likely to have need thereof, and in particular in the leather and textile industry, in perfumery, in the agri-food industry, etc.

Preferentially, the formate and/or formic acid obtained from such a microbiological process is used in a secondary biological process (in situ or ex situ) to obtain organic compounds of higher added value, and in particular methane, lactate or $C_1$-$C_5$ alcohols. Alternatively, it is possible to directly use the reaction medium containing the formate and/or formic acid obtained for the implementation of the secondary biological process. If the compounds obtained are alcohols, a stripping process carried out by bubbling $CO_2$-containing gas can be used to continuously recover the alcohols produced.

In a particular embodiment, it is possible, prior to the reaction step, to co-culture *Stenotrophomonas maltophilia* with one or more other methanotrophic bacterial species. It is thus possible to produce organic nutrients from methane, said nutrients then being used by *Stenotrophomonas maltophilia* as a source of carbon and energy. For example, the inventors have demonstrated that co-culture under a methane/air mixture and on a mineral medium of *Stenotrophomonas maltophilia* with a methanotrophic bacterium, such as *Methylosinus trichosporium* OB3b, allows the production of acetate that can be used by *Stenotrophomonas maltophilia* for its growth. The inventors have further shown that the presence of such a methanotrophic bacterium in the liquid phase during the subsequent reaction step does not disrupt the reduction of $CO_2$ or the production of formate and/or methane by *Stenotrophomonas maltophilia*.

Alternatively or additionally, it is possible during the reaction step (i.e. bringing *Stenotrophomonas maltophilia* into contact with the $CO_2$-containing gas phase) to add to the liquid phase one or more other microorganisms, and in particular bacteria, archaea and/or yeasts, capable of using the formate to produce molecules with higher added value. It is also possible to co-culture *Stenotrophomonas maltophilia* with one or more of these microorganisms prior to the reaction step, and then to add all the microorganisms obtained to the liquid reaction medium for the reaction step. In an embodiment, the bacterium *Microbacterium oxydans* is added to *Stenotrophomonas maltophilia*. In an embodiment, hydrogenotrophic methanogenic archaea are added to obtain methane. In an embodiment, the bacterium *Ralstonia eutropha* H16 (LH74D) is added to *Stenotrophomonas maltophilia* in order to obtain $C_4$-$C_5$ alcohols. In an embodiment, a methanotrophic bacterium and a methanol dehydrogenase inhibitor are added to *Stenotrophomonas maltophilia* in order to obtain methanol.

Alternatively, the step of $CO_2$ reduction reaction to formate by *Stenotrophomonas maltophilia* is carried out in a first reactor, and the formate produced is recovered to feed a second reactor in which are located the microorganism(s) capable of using the formate to produce molecules with higher added value. The second reactor can be fed directly with the reaction medium of the first reactor, containing the formate produced, or conversely contain a medium to which is added the formate extracted from the reaction medium of the first reactor.

Another object of the invention is the use of *Stenotrophomonas maltophilia*, for the production of formate and/or methane and/or any other product whose carbon oxidation number is lower than that of $CO_2$ by $CO_2$ reduction as described above. The use of *Stenotrophomonas maltophilia* consumes significant amounts of $CO_2$ and thus addresses the environmental problems related to the accumulation of $CO_2$ in the atmosphere while adding value to the $CO_2$ consumed.

Other aspects and advantages of the present invention will become apparent in the following experimental section, which should be considered for illustrative purposes, without in any way limiting the scope of the protection sought.

EXAMPLES

A] Materials and Methods
1. Culture of the Bacterium *Stenotrophomonas maltophilia*

Two routes of *S. maltophilia* culture were implemented:
(i) Aerobic Co-Culture with the Methanotrophic Bacterium *Methylosinus trichosporium* OB3b In this case, the source of carbon and energy used is methane, which is converted by the methanotrophic bacterium into organic nutrients that can be assimilated by the bacterium *S. maltophilia* for its growth. In particular, acetate, at a concentration of about 35 mg·L$^{-1}$, is measured in the culture reactor at the end of growth. Such a synergy between these two types of bacteria has already been reported in nature and for a consortium involving them, the production of acetate by methanotrophs has already been demonstrated under oxygen-limited conditions (C. Costa et al., Denitrification with methane as electron donor in oxygen-limited bioreactors, *Appl. Microbiol. Biotechnol.*, 53(6) (2000) 754-762).

The culture medium is a mineral medium enriched with copper and iron. The basal medium is composed of: 1.06 g/L $KH_2PO_4$, 4.34 g/L $Na_2HPO_4.12H_2O$, 1.7 g/L $NaNO_3$, 0.34 g/L $K_2SO_4$ and 0.074 g/L $MgSO_4.7H_2O$. Once prepared, the pH of this basal medium is adjusted to 7.0±0.1 with 0.1 M NaOH or 0.1 M HCl, and then autoclaved. The mineral, copper and iron solutions are prepared independently and sterilized by filtration through cellulose acetate filters with a pore diameter of 0.2 µm before being added to the basal medium. Final mineral concentrations are: 0.57 mg/L $ZnSO_4.7H_2O$, 0.446 mg/L $MnSO_4.H_2O$, 0.124 mg/L $H_3BO_3$, 0.096 mg/L $Na_2MoO_4.2H_2O$, 0.096 mg/L KI and 7.00 mg/L $CaCl_2.2H_2O$. Final copper and iron concentrations are: 0.798 mg/L $CuSO_4$ and 11.20 mg/L $FeSO_4.7H_2O$.

The cultures are conducted in sealed closed reactors, incubated at 30° C. and under constant rotation (160 rpm). The headspace of the reactors is filled with a mixture of air and methane (1:1 v/v); the volume of gas is three times that of the liquid. The inoculation percentages of *S. maltophilia* can vary from 10 to 50% v/v. Cultures are stopped when the optical density at 600 nm ($OD_{600\ nm}$) is constant.

Two successive cultures are conducted before implementing the consortium for the $CO_2$ reduction reaction.
(ii) Pure Aerobic Culture of the Biocatalyst The bacterium *S. maltophilia* was first isolated from a consortium formed with the bacterium *M. trichosporium* OB3b (obtained according to the protocol described above). The isolation was carried out by successive subcloning of *S. maltophilia* colonies on Lysogeny Broth (LB) Miller agar medium (Sigma Aldrich, France). The purity and identification of the isolated bacterium were confirmed by biochemical analyses (see point 2 below). The strain is preserved on LB agar plates stored both at 4° C. and in the freezer at −20° C. in its native liquid culture medium to which glycerol (20% v/v) is added. The culture reactor is a closed reactor with an air-permeable plug which is dedicated to sterile cultures. An LB liquid culture medium is inoculated with *S. maltophilia*, 5% v/v from a frozen aliquot or with all the colonies from an agar plate, then incubated for 24 h at 30° C. and under constant rotation (160 rpm). Cultures are stopped when the stationary phase starts ($OD_{600\ nm}$ is constant).

Two successive cultures are carried out before using the biocatalyst for the $CO_2$ reduction reaction.

A correlation between the $OD_{600\ nm}$ (–) and the mass concentration [X] of *S. maltophilia* ($g_{day\ cells} \cdot L^{-1}$) is established to determine formate productivities; the correlation is obtained on the basis of five independently replicated points:

$$[X](g_{dry\ cells} \cdot L^{-1}) = 0.3035 \times OD_{600\ nm}\ (R^2 = 0.995)$$

2. Biochemical Analyses

The *Stenotrophomonas maltophilia* isolate derived from co-culture was first characterized with Gram stain and by mass spectrometry. Gram staining showed that the isolate is a Gram-negative *bacillus*. Mass spectrometry analysis confirmed that the isolate was pure and identified the bacterium *S. maltophilia*, which is indeed a Gram-negative *bacillus*. In mass spectrometry, it should be noted that a score above 1.90 indicates reliable identification and that the score obtained for *S. maltophilia* is 2.18. Before each culture, a qualitative analysis of the *S. maltophilia* colonies spread on agar plates is performed in order to detect possible contamination. Furthermore, 16S RNA sequencing of the isolate confirmed that the identified bacterium is indeed *Stenotrophomonas maltophilia*.

3. Preparation of the Bacterial Suspension Used in the $CO_2$ Reduction Tests

At the end of the culture, the cells are collected by centrifugation at 4° C. and 4000 g for 20 min. They are then resuspended in 20 mM phosphate buffer at pH 7.0 and centrifuged again under the same conditions as before and the bacterial pellet is recovered. A reaction medium containing 20 mM phosphate buffer at pH 7.0 and 5 mM $MgCl_2$ is used to resuspend the bacterial pellet and obtain an $OD_{600\ nm}$ of (i) 10.3±0.5 (i.e. 3.1±0.2 $g_{cells}/L$) for closed reactor assays and (ii) 6.6±0.3 (i.e. 2.0±0.1 $g_{cells}/L$) for electrolysis-assisted tests. A sample of the prepared suspension is always stored at –20° C. with glycerol (20% v/v) for possible subsequent biochemical analyses. The remainder of the suspension is used immediately for $CO_2$ reduction tests. The reaction medium does not contain any organic nutrients allowing the growth of the biocatalyst, which is this used as a resting cell.

4. $^{13}CO_2^3$ Reduction Tests in a Closed Reactor

The bacterial suspension obtained in the preceding step is distributed into sealed 60 mL reactors by adding 6 mL of suspension to each reactor. In order to evaluate the ability of the biocatalyst to reduce $CO_2$, the headspace is filled with a gas mixture containing $^{13}CO_2$ which is sterilized by filtration through Teflon filters with a 0.2 μm pore diameter. Different gas mixtures were tested: $^{13}CO_2$:atmospheric air (3:7 v/v), $^{13}CO_2$: $N_2$ (3:7 v/v) and pure $^{13}CO_2$. For each experiment, a set of several reactors was prepared under identical conditions and incubated at 30° C. with constant stirring (160 rpm). Each kinetics is followed for more than 20 days and up to 35 days; to this end, at each sampling time, one reactor is sacrificed for analysis. Different measurements are carried out: optical density at 600 nm ($OD_{600\ nm}$), pH, formate determination by gas chromatography coupled with mass spectrometry (GC-MS), characterization of the gas composition of the headspace by GC-MS, determination of intracellular poly-3-hydroxybutyrate (PHB) by GC-MS and determination of ammonium ions ($NH_4^+$) by ion chromatography (IC). The products derived from $^{13}CO_2$ are detected in the reaction medium and in the headspace by GC-MS and NMR. Counts of viable bacteria are also carried out at the beginning and end of the kinetics; to this end, samples are cultured under autotrophic aerobic conditions. Finally, blanks prepared with the reaction medium alone (without bacteria) under a $^{13}CO_2$:atmospheric air mixture (3:7 v/v) showed no contamination over the duration of the tests, confirming the sterility of the closed reactor tests.

5. $CO_2$ Reduction Tests in a Semi-Closed Reactor, Assisted by Electrolysis

A glass reactor is used. Its useful liquid volume is 60 mL and its headspace represents about 40% of its total volume. A lid is screwed onto the reactor and the tightness of the lid-reactor junction is guaranteed by a gasket. This lid has an inlet port for the gas supply (100% $^{12}CO_2$) which is made at the core of the solution by a gas distributor, a port for the gas outlet and 3 ports for the positioning of the electrodes. The reactor is thermostatically controlled at 30° C. under constant stirring (300 rpm).

The electrochemical system is a conventional device with 3 electrodes (working electrode, reference electrode and counter electrode). The working electrode (or cathode) is a graphite coupon with a surface area of 2.5 cm×2.5 cm and a thickness of 0.5 cm (Goodfellow), electrically connected with a titanium rod (Goodfellow). Before each experiment, the graphite coupon is washed for 1 h in a 1 N HCl solution to dissolve any adsorbed species, then in a 1 N NaOH solution to neutralize the acidity and finally rinsed with sterile ultrapure water before being left overnight in 1 L of sterile ultrapure water to drive out any soda residue included in the graphite pores. The titanium rod is cleaned with acetone and then autoclaved. In this device, the ratio of the active surface of the cathode to the volume of the reactor is thus 10.4 $m^2/m^3$; where the active surface is defined as the geometrical surface exposed to the counter-electrode.

The counter-electrode (or anode) is a platinum grid, previously cleaned and disinfected by flame. In this device, the ratio of the projected geometrical surface of the anode to that of the cathode is about 1.5 so as not to limit the cathodic phenomena.

The potentials are monitored and expressed in relation to an Ag/AgCl reference electrode (potential of 0.240 V/ESH, Radiometer analytical).

The polarization potential of the working electrode is applied with a one-channel potentiostat (Ametek VersaSTAT3) and the current is recorded every 900 s. Chronoamperometry (CA) is periodically stopped to acquire cyclic voltammetries (CVs) between –1.2 and 1.0 V vs Ag/AgCl, at a sweep rate comprised between 1 and 10 $mV \cdot s^{-1}$. It should be recalled that a cyclic voltammetry (or cyclic voltamperometry) consists in performing a potential sweep at the working electrode and measuring the current flowing in the electrochemical system. This technique makes it possible to: (i) check the coherence of the CA with the CV, (ii) acquire kinetic information on the system and (iii) detect redox compounds in the suspension.

First, the reactor is filled with a bacterial suspension of *S. maltophilia* in reaction medium (prepared according to 2.c), in which a continuous bubbling of 100% $CO_2$ or a $CO_2$:$CH_4$ gas mixture (1:1 or 1:2 v/v) is carried out at a flow rate comprised between 2 or 25 $ml \cdot min^{-1}$. Then a polarization ranging from –0.7 V to –1.0 V vs Ag/AgCl is applied. Polarization is started at the same time as chronoamperometry. In parallel, a control reactor without electrodes (and thus without polarization) is implemented in the same way as the electrochemical reactor. Samples are taken over time, under a microbiological hood, to measure the optical density at 600 nm ($OD_{600\ nm}$) and the pH of the liquid medium; the pH was found to be constant and equal to 6.4±0.2 (corresponding to the pKa of the $CO_2,H_2O/HCO_3^-$ pair). The gas composition is analyzed at the reactor inlet and outlet by gas chromatography coupled with a katharometer (GC-TCD) to determine the experimental flow of reduced $CO_2$.

6. Physicochemical Analyses

Liquid Sample Processing

The complete reaction medium (with bacteria) and the supernatant (without bacteria) are analyzed. The complete reaction medium is either directly analyzed or frozen at $-20°$ C. upon collection for subsequent analysis. The supernatant is obtained by centrifugation of the complete reaction medium just collected; the centrifugation is conducted for 10 min at 10 000 g and 10° C. and the supernatant is collected as soon as the centrifugation is completed for immediate analysis or freezing at $-20°$ C. The pellet is stored at $-20°$ C. for subsequent analysis.

Analyses Performed by Nuclear Magnetic Resonance (NMR):

For these analyses, 500 μL of liquid sample (reaction conducted with $^{13}CO2$, 2.d) is introduced into a 5 mm diameter NMR tube with 50 μL of $D_2O$ and then analyzed by a BRUKER NMR Avance III—500 MHz—CryoProbe Helium for 4 hours. Different standards (labeled and unlabeled sodium formate, sodium acetate, methanol, ethanol, formaldehyde, acetaldehyde, sodium lactate, glycerol, isobutanol, sodium succinate, sodium fumarate, sodium pyruvate, sodium oxaloacetate) prepared in the reaction medium were first analyzed by NMR to obtain the fingerprints of these molecules. On this apparatus, the detection threshold of $^{13}C$-labeled molecules is 6 mg·L$^{-1}$. However, NMR analyses can only detect $^{13}C$ isotopes which have a relative abundance of 1.1% compared with their $^{12}C$ isotope in nature [W. Mook and P. Grootes, International Journal of mass Spectrometry and ion Physics, 1973, 12(3): p. 273-298]. Consequently, a concentration of $^{13}C$ unlabeled product of about 600 mg·L$^1$ is needed to detect these compounds.

Analyses Carried Out by Gas Chromatography Coupled with Mass Spectrometry (GC-MS):

Equipment

Gas chromatography (Clarus 580, Perkin Elmer) is conducted with a capillary column (30 m×0.25 mm ID, film thickness 8 μm, Rt-Q-Bond Plot, Restek), coupled with mass spectrometry (Clarus SQ-8-MS, Perkin Elmer) equipped with a quadrupole mass selective electronic impact (EI) detector operated at 70 eV. A sample changer (Turbomatrix Headspace 16S, Perkin Elmer) is used for the injection of headspace obtained after heating liquid samples to 100° C. For the analysis of the composition of the headspace of the closed reactor maintained at 30° C., the samples are taken directly from the reactor with a gas-tight syringe and manually injected into the GC-MS. Helium is used as carrier gas at a flow rate of 1.5 ml/min.

Determination of $^{12}C$-Formate and $^{13}C$ Formate in the Liquid Samples

An esterification method based on the protocol described by Wallage et al (2008) (Formic acid and methanol concentrations in death investigations, *Journal of Analytical Toxicology*, 32 (2008) 241-248) was used for the quantification of formate. The esterification reaction is carried out between the organic acid present in the liquid sample and the methanol added under acidic conditions. In a GC-MS analysis vial (22 mL), 600 μL of sample, 100 μL of acetonitrile (157.2 mg·L$^{-1}$) as internal standard, 100 μL of concentrated sulfuric acid and 100 μL of methanol as derivatizing agent are introduced in this order. The test vial is then placed in the autosampler and heated at 100° C. for 15 minutes in order to complete the esterification reaction. In the case of the analysis of the complete medium (with bacteria), a spreading of the mixture on agar made it possible to verify that these conditions allow the lysis of the bacteria because no re-growth was detected. The temperature of the injector is set at 200° C. and the split at 1:16. In the oven, a temperature gradient is achieved from 40 to 150° C., at a rate of 10° C./min. The ions detected, in single ion recording (SIR) mode, correspond to one of the mass/charge ratios m/z of 60 for $^{12}C$-methyl formate and 41 for acetonitrile. In order to determine whether the carbon is $^{12}C$ or $^{13}C$, [M+1] was also evaluated for $^{13}C$-methyl formate (m/z of 61). The presence of labeled species is only considered for levels significantly above 1%, which therefore exceed the percentage related to natural isotope abundance. Calibration curves were first established with formate and acetate standards: Na(HCOO) and Na(H$^{13}$COO) obtained from Sigma-Aldrich.

Analysis of Gases in the Headspace of the Closed Reactor

The headspace of the closed reactor is analyzed to determine the gaseous species, labeled with $^{13}C$ or not, present over time. For each analysis, 250 μL of headspace is taken from the reactor incubated at 30° C. using a gas-tight syringe and 50 μL is injected into the GC-MS. The temperature of the injector is set at 200° C. and the split at 1:16. In the oven, a temperature gradient is achieved from 100 to 150° C., at a rate of 10° C./min. In SIR mode, the ions detected are m/z 28 ($N_2$), m/z 44 ($CO_2$), m/z 45 ($^{13}CO_2$), m/z 16 ($^{12}CH_4$) and m/z 17 ($^{13}CH_4$).

Determination of Ammonium Ions ($NH_4^+$) by Ion Chromatography (IC)

$NH_4^+$ ions are determined in the supernatants. The analysis is performed by injecting 25 μL of sample into a Dionex ICS-1000 (Thermo Scientific) chromatographic device equipped with an IonPAc AS19 (0.4×250 mm) capillary column. The elution program is as follows: 10 mM KOH (from 0 to 10 min), then 10-45 mM KOH (from 10 to 30 min).

Analyses Carried Out by Gas Chromatography Coupled to a Katharometer (GC-TCD)

Equipment

Gas chromatography (Clarus 580, Perkin Elmer) is conducted with a PE-Q column (Perkin Elmer, 30 m) in series with a PE-MOLESIEVE molecular sieve column (Perkin Elmer, 30 m) coupled to a thermal conductivity detector, also called a katharometer (Perkin Elmer). A 10-way loop valve is used to load and inject the gas samples.

Analysis of the Composition of Gases, Labeled or not

For each analysis, a minimum of 20 mL of gas to be analyzed is sent through the loop valve and 20 μL of sample is injected into the columns. Helium is the carrier gas at a flow rate of 10 mL·min$^{-1}$. In the oven, a temperature gradient is achieved from 40° C. to 120° C. at a rate of 10° C.·min$^{-1}$. A calibration is performed to determine the $CO_2$.

Determination of the Mass % of Intracellular PHB

The method based on PHB digestion and analysis of its monomer (3-hydroxybutyrate) by GC-MS (A. J. Pieja et al, Applied and environmental microbiology, 2011: p. AEM.00509-11; G. Braunegg et al., European journal of applied microbiology and biotechnology, 1978, 6(1): p. 29-37) was implemented, with the difference that the bacterial pellets were frozen instead of being lyophilized before the PHB digestion step.

Bacterial pellets stored at $-20°$ C. are thawed at room temperature and then digested for 3 h at 100° C. in 2 mL of methanol containing 3% concentrated sulfuric acid and 0.1% benzoic acid to which 2 mL of chloroform is added. Re-growth tests on LB medium showed that the bacteria contained in the pellets and treated by this acid digestion were totally inactivated. Once the sample is cooled, 1 mL of demineralized water is added to induce phase separation. The aqueous phase is then removed and 2 μL of organic phase is injected into the GC-MS. Analyses are conducted with the same GC-MS apparatus as that used for formate analysis. A DB-1 column (Agilent J&W) is used for the separation. The carrier gas is helium at a flow rate of 32 mL·min$^{-1}$. The oven temperature is programmed at 80° C. for 1 min, up to 120° C. at a rate of 10° C./min, then the temperature is increased to 270° C. at a rate of 45° C./min. The temperature of the injector is set at 200° C. and the split at 30 mL/min.

The use of a PHB standard (Sigma Aldrich) makes it possible to establish a calibration curve giving the ratio of the areas of 3-hydroxybutyrate and benzoate peaks as a function of the mass of PHB introduced.

Peak area ratio (3-hydroxybutyrate/benzoate)
=0.1675×$m_{PHB}$ ($R^2$=0.9865)

To determine the mass % of intracellular PHB per unit mass of dry cells ($w_{PHB}/w_{dry\ cells}$) in the samples, the PHB mass measured in the sample by the method described above is divided by the dry mass of bacteria present which is known from $OD_{600}$ measurements.

B] Results

I. $^{13}CO_2$ Reduction Tests in a Closed Reactor

In order to evaluate the ability of the biocatalyst to reduce $CO_2$, $^{13}C$-labeled $CO_2$ is used. The purpose of $CO_2$ labeling is to detect the labeled products derived from $^{13}CO_2$ and to distinguish them from those derived from a simple cellular release. To identify these products, the NMR technique is used to analyze the bacterial suspension and its supernatant while the GC-MS technique is used to characterize the reactor headspace. Moreover, this labeling makes it possible to observe the NMR and GC-MS fingerprints of all products having one or more $^{13}C$ that may result (i) from the reduction of $^{13}CO_2$ and/or (ii) from the fixation of $^{13}CO_2$ by the cell. The optical density at 600 nm ($OD_{600\ nm}$) is measured over time to monitor the change in the bacterial mass concentration (in $g_{dry\ cells}/L$). Viable cell counts are also performed to access the bacterial cell concentration (in CFU/mL) and the pH is measured during the reaction. The ammonium ion ($NH_4^+$) content in the reaction medium is monitored to study the influence of the presence of ammonium on the performance of the $CO_2$ reduction bioprocess.

1. Monitoring of $^{13}CO_2$ Assimilation Metabolism by NMR and GC-MS

The bacterial suspension of Stenotrophomonas maltophilia is brought into contact with a gaseous atmosphere $^{13}CO_2$:atmospheric air (1:1 v/v). FIG. 1 shows the NMR spectra obtained on the complete bacterial suspension (a) initially (start of reaction), (b) after 8 days of reaction and (c) after 35 days of reaction.

From the start of the reaction, two peaks are visible: that of $^{13}CO_2$ (chemical shift δ=124.6 ppm) and that of $H^{13}CO_3^-$ (chemical shift δ=160.2 ppm). After 8 days of reaction, a peak with a chemical shift corresponding to that of $^{13}C$-formate (δ=171.0 ppm) appears.

In order to verify that this peak indeed corresponds to the labeled $^{13}C$-formate ($H^{13}COO$), a small amount of $^{13}C$-formate standard is added to the sample (at a final concentration of 10 mg/L). The amplitude of the peak increased when the standard was added, confirming that this peak is indeed attributable to $^{13}C$-formate. No compounds other than $^{13}C$-formate are detected by NMR, suggesting that $^{13}C$-formate is the result of a direct reduction of $^{13}CO_2$.

Indeed, $^{13}C$-formate has a single carbon, at a lower oxidation state than $^{13}CO_2$. Blanks made without bacteria under the same conditions (i.e. under $^{13}CO_2$/atmospheric air mixture) show no labeled compounds, except $^{13}CO_2$ and $H^{13}CO_3^-$, thus confirming the role of bacteria on the reduction of $^{13}CO_2$ to $^{13}C$-formate.

The reduction kinetics of $^{13}CO_2$ by the bacterium Stenotrophomonas maltophilia is reproduced and the liquid medium of the reactor is also analyzed at 35 days (FIG. 1.c). The peaks corresponding to $^{13}CO_2$ and $H^{13}CO_3^-$ are still visible at 35 days, revealing that there is no $CO_2$ limitation. Only the peak corresponding to $^{13}C$-formate (δ=171.0 ppm) is still visible. This means that the $^{13}C$-formate produced is not used by the bacterium to form new compounds and that $^{13}CO_2$ is likely the final electron acceptor. These new tests confirmed that the presence of the bacterium S. maltophilia can catalyze the reduction reaction of $^{13}CO_2$ to $^{13}C$-formate in the liquid phase.

Furthermore, GC-MS analysis of the headspace of several closed reactors reveals the presence of labeled methane ($^{13}CH_4$) in significant amounts after 34 days. Under the conditions tested, the content of this gas nevertheless remains below 1% v/v. Like $^{13}C$-formate, $^{13}CH_4$ is a single-carbon compound with a lower oxidation state than $^{13}CO_2$. This $^{13}CH_4$ is therefore derived from the reduction of $^{13}CO_2$, either directly ($^{13}CO_2 \rightarrow ^{13}CH_4$) or indirectly ($^{13}CO_2 \rightarrow ^{13}C$-formate $\rightarrow ^{13}CH_4$). Methane is a particularly attractive product because it can be easily recovered by stripping and used as fuel.

In conclusion, the bacterium S. maltophilia is capable of reducing $CO_2$ to formate and methane. In order to quantify the production of $^{13}C$-formate in the liquid reaction medium, $^{13}CO_2$ reduction tests are reproduced under similar conditions, considered as reference conditions. The $^{13}C$-formate concentration is this time determined by GC-MS; in addition, the optical density at 600 nm ($OD_{600}$) and pH are also monitored.

2. $^{13}CO_2$ Reduction Tests in a Closed Reactor Under Reference Conditions a. Definition of Reference Conditions The reference conditions are defined as follows: initial bacterial concentration of 3.1±0.2 $g_{dry\ cells}/L$, initial gaseous atmosphere composed of a $^{13}CO_2$ atmospheric air mixture (3:7 v/v), aqueous reaction medium composed of 20 mM phosphate and 5 mM $MgCl_2$. Three independent kinetics are conducted in parallel under these reference conditions.

b. Monitoring of Biomass Concentration and pH

The bacterial mass concentration, denoted [X], is monitored by measuring $OD_{600}$. The correlation giving the $OD_{600}$ as a function of bacterial mass concentration is given in section A.1]. For all three kinetics monitored, a decrease in biomass concentration is observed (data not shown). The most likely reason to explain this phenomenon is cell lysis. Indeed, a lack of natural nutrients and a $CO_2$-rich atmosphere exposes bacterial cells to stressful conditions, which are likely to lead to the death and thus cell lysis of part of the bacterial population. Throughout the kinetics, however, no test shows total lysis. Indeed, for all experiments, the cell mass concentration, initially of 3.1±0.2 $g_{dry\ cells}\cdot L^{-1}$, falls over the first 10 days and then stabilizes at a mean value of 0.5±0.1 $g_{dry\ cells}/L$. This means that only part of the biocatalyst suspension lyses during the first 10 days of the kinetics and then the mass concentration remains stable.

In addition, the counting of viable cells in the bacterial suspension after 35 days confirms on the one hand that cell lysis is occurring and on the other that 15±4×10$^4$ CFU/mL are still viable; the initial concentration being 60×10$^7$ CFU/ mL. The concentration of viable cells has therefore decreased significantly but still remains high (of the order of $10^5$ CFU/mL). It is hypothesized that this cell lysis may be a way for the bacteria to adapt to its new conditions thanks to the organic compounds released in the medium by the lysis of cells (J. M. Navarro Llorens et al., FEMS microbiology reviews, 2010, 34(4): p. 476-495).

During these kinetics, the pH is also monitored (data not shown). Regardless of the experiment, the change in pH is very similar. Indeed, the initial pH is set at 7.0±0.1 and for all the tests, the pH decreases to an average value of 6.4±0.2 over the first 5 days and then remains constant at this value which corresponds to the pKa of the acid-base pair $CO_2$, $H_2O/HCO_3^-$ induced by the dissolution of $CO_2$ in the reaction medium. The pH of the medium is thus buffered throughout the kinetics.

c. Monitoring of $^{13}C$-Formate Production in the Liquid

Figure 2:
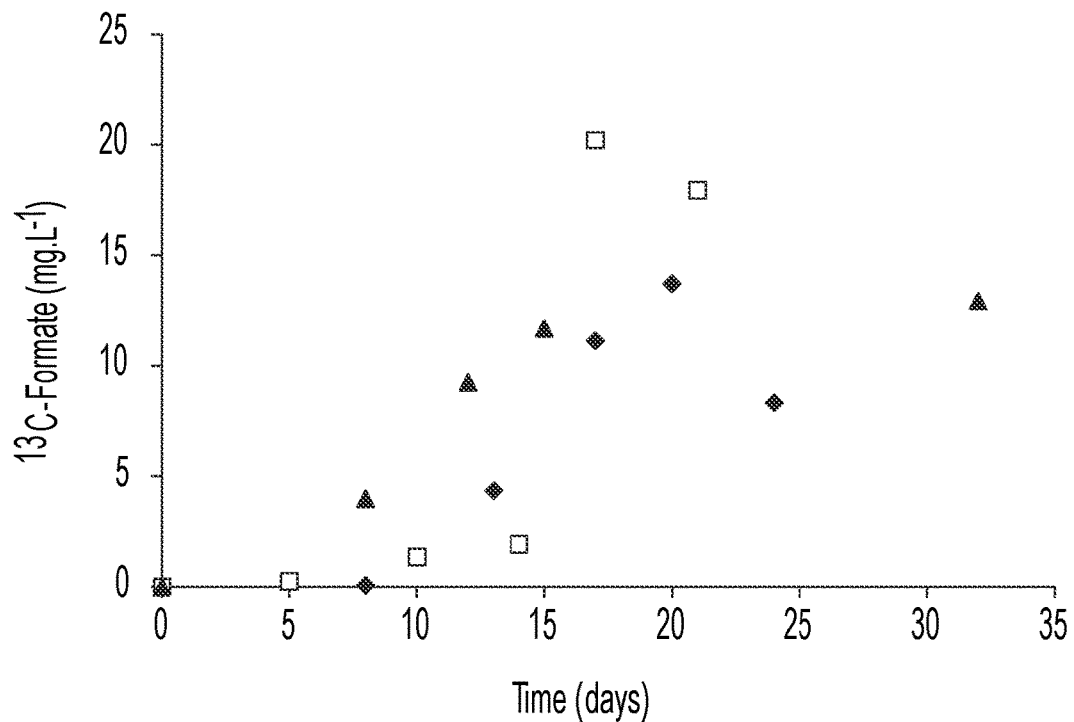
FIG. 2. $^{13}$C-formate production kinetics obtained during $^{13}CO_2$ reduction tests conducted in a closed reactor and under reference conditions with the bacterium Stenotrophomonas maltophilia. Each color represents an independent test.

The $^{13}C$-formate production from $^{13}CO_2$ reduction is quantified by GC-MS and its change over the three different kinetics is presented in FIG. 2.

Regardless of the kinetics, $^{13}C$-formate is produced in significant amounts. Furthermore, GC-MS analysis has shown that $^{13}C$-formate is found in complete suspensions (i.e. in the presence of bacteria) but not in the respective supernatants. This shows that the production of this $^{13}C$-formate is carried out by the intact bacteria remaining in the reaction medium and not by free enzymes from cell lysis. The $^{13}C$-formate appears after only 8 to 10 days, a period which may correspond to a latency phase during which the bacteria adapt to its new $^{13}CO_2$ substrate. The fact that a high concentration of bacteria (close to $10^5$ CFU/mL) is still viable at the end of the kinetics confirms the presence of bacteria maintaining metabolic activity.

The $^{13}CO_2$ thus enters the cells, either in the $^{13}CO_2$ form or in the $H^{13}CO_3^-$ form; indeed, the pH stabilizes around the pKa of the $CO_2,H_2O/HCO_3^-$ pair and the two forms thus coexist in close proportions. Then the cells having survived the reaction conditions and lysis thus use one of their intracellular enzymatic system to catalyze the reaction of reduction of this $^{13}CO_2$ to $^{13}C$-formate. Two families of enzymes, potentially present inside the bacterium S. maltophilia, are likely to catalyze this $CO_2$ reduction reaction to formate: the formate dehydrogenases (FDHs) and the nitrogenases. At present, these enzymes are first isolated from their native microorganism and then purified before being used (L. B. Maia et al., Inorganica Chimica Acta, 2017, 455: p. 350-363; Khadka et al. 2016, Inorg. Chem., 55, 8321-8330).

It should be stressed that the maximum formate concentrations produced (10-20 mg·L$^{-1}$, FIG. 2) are lower than the theoretical maximum $^{13}C$-formate concentration that could have been achieved if all the $^{13}CO_2$ present in the reactor had been reduced (i.e. 4.6 g·L$^{-1}$). This calculation is based (i) on the number of moles of $^{13}CO_2$ introduced into the headspace (obtained by the law of perfect gases) and (ii) on a 1:1 stoichiometry with respect to $^{13}CO_2$ and formate (i.e., assuming that one mole of $^{13}CO_2$ gives one mole of $^{13}C$-formate). This therefore suggests that there is no macroscopic limitation to the transfer of $^{13}CO_2$ into the liquid phase containing the bacteria. However, a microscopic limitation of $^{13}CO_2$ transport from the core of the liquid to the biocatalyst is not excluded. Indeed, the presence of free DNA from the observed cell lysis could create significant resistance to mass transfer in cells. A study has already reported this type of phenomenon for the bacterium E. coli (Castan et al., John Wiler & Sons, Inc. Biotechnol. Bioeng. 77 (2002) 324-328), which has similarities with the bacterium S. maltophilia, because it is also an aerobic Gram-negative bacillus-like bacterium. In the study by Castan et al. the presence of free DNA would limit the mass transfer of dissolved oxygen ($O_2$) to the cells. In the present case, such a limitation could also occur for dissolved $^{13}CO_2$. A solution to increase formate production would be to supply $CO_2$ to the core of the solution through a gas distributor. Furthermore, the concentration of bacteria and the specific $CO_2$-reducing activity of the cells may also be limiting elements in the reduction reaction. It is therefore possible to adjust these parameters to optimize the flow of reduced $CO_2$.

d. Production $P_{formate}$ of $^{13}C$-Formate and Volume Flow $F_{CO2,vol}$ of Reduced $^{13}CO_2$ Regardless of the kinetics considered (FIG. 2), the production of $^{13}C$-formate $P_{formate}$, in mg $^{13}C$-formate·$(g_{dry\ cells})^{-1}$·$d^{-1}$ or µmol $^{13}C$-formate·$(g_{dry\ cells})^{-1}$·$d^{-1}$, is defined as:

$$P_{formate} = \Delta C/\Delta t/C_{bacteria} \quad \text{(Equation 4)}$$

with $\Delta t$: production period (days),
$\Delta C$: difference in $^{13}C$-formate concentration over the production period (mg·L$^{-1}$ or µmol·L$^{-1}$),
$C_{bacteria}$: bacterial concentration initially introduced ($C_{bacteria}$=3.1±0.2 $g_{dry\ cells}$·L$^{-1}$) to take into account the bacterial supply required.

Similarly, if it is considered that one mole of $^{13}C$-formate produced corresponds to one mole of reduced $^{13}CO_2$, then the flow $FCO_2$ of reduced $^{13}CO_2$ in µmol $^{13}CO_2$·$(g_{dry\ cells})^{-1}$·$d^{-1}$ will therefore be equal to the formate production $P_{formate}$ expressed in µmol $^{13}C$-formate·$(g_{dry\ cells})^{-1}$·$d^{-1}$. The volume flow $F_{CO2,vol}$ of reduced $^{13}CO_2$ expressed in mL $^{13}CO_2$·$(g_{dry\ cells})^{-1}$·$d^{-1}$ will be calculated according to the following equation:

$$F_{CO2,vol} = F_{CO2} \cdot v_m \quad \text{(Equation 5)}$$

where $v_m$ is the molar volume at 30° C. of the $^{13}CO_2$ assumed to be perfect gas (25.19 $10^{-3}$ mL·µmol$^{-1}$).

Table 1 details the values of $\Delta C$ and $\Delta t$ for each of the three kinetics presented above, as well as the productions of $^{13}C$-formate ($P_{formate}$) and the flows of reduced $^{13}CO_2$ ($F_{CO2,vol}$).

TABLE 1

Production of $^{13}C$-formate ($P_{formate}$) and flows of reduced $^{13}CO_2$ ($F_{CO2,vol}$) obtained in a closed reactor

| Kinetics | $\Delta C$ (mg·L$^{-1}$) | $\Delta t$ (j) | $P_{formate}$ (mg $^{13}C$-formate·$(g_{dry\ cells})^{-1}$·$d^{-1}$) | $P_{formate}$ (µmol $^{13}C$-formate·$(g_{dry\ cells})^{-1}$·$d^{-1}$) | $F_{CO2,vol}$ (mL $^{13}CO_2$·$(g_{dry\ cells})^{-1}$·$d^{-1}$) |
|---|---|---|---|---|---|
| 1 (blue) | 9.4 | 7 | 0.5 | 10.0 | 0.3 |
| 2 (red) | 18.8 | 7 | 0.9 | 20.0 | 0.5 |
| 3 (green) | 7.7 | 7 | 0.4 | 8.2 | 0.2 |

TABLE 1-continued

Production of $^{13}$C-formate ($P_{formate}$) and flows of reduced $^{13}CO_2$ ($F_{CO2, vol}$) obtained in a closed reactor

| Kinetics | ΔC (mg · L$^{-1}$) | Δt (j) | $P_{formate}$ (mg $^{13}$C-formate · ($g_{dry\ cells}$)$^{-1}$ · d$^{-1}$) | $P_{formate}$ (µmol $^{13}$C-formate · ($g_{dry\ cells}$)$^{-1}$ · d$^{-1}$) | $F_{CO2, vol}$ (mL $^{13}CO_2$ · ($g_{dry\ cells}$)$^{-1}$ · d$^{-1}$) |
|---|---|---|---|---|---|
| Average | 11.8 ± 5.6 | 7 | 0.6 ± 0.3 | 12.7 ± 6.3 | 0.3 ± 0.2 | e. Production of $^{13}$C-Formate from $^{13}CO_2$: Reproducibility Study

In order to study the reproducibility of this bioprocess, six other independent $^{13}CO_2$ reduction tests were conducted under reference conditions, using bacterial suspensions prepared from different *S. maltophilia* cultures. For each of these tests, a significant production of $^{13}$C-formate was demonstrated. Applying the calculations in the previous section (Eq. 4 and 5) to the results obtained during these kinetics (6 in total), a mean production $P_{formate}$ of 9.1 µmol $^{13}$C-formate·($g_{dry\ cells}$)$^{-1}$·d$^{-1}$ was obtained (i.e. 0.4 mg formate·($g_{dry\ cells}$)$^{-1}$·d$^{-1}$), with a minimum and maximum respectively of 2.3 and 30 µmol $^{13}$C-formate·($g_{dry\ cells}$)$^{-1}$·d$^{-1}$ (i.e. 0.1 and 1.4 mg $^{13}$C-formate·($g_{dry\ cells}$)$^{-1}$·d$^{-1}$).

Similarly, a mean volume flow $F_{CO2,vol}$ of reduced $^{13}CO_2$ of 0.24 mL $^{13}CO_2$·($g_{dry\ cells}$)$^{-1}$·d$^{-1}$ was obtained, with a minimum and maximum respectively of 0.06 and 0.76 mL $^{13}CO_2$·($g_{dry\ cells}$)$^{-1}$·d$^{-1}$; these differences in flow being certainly related to the differences in physiological state of the bacteria used for the $^{13}CO_2$ reduction tests.

f. Production of $^{13}H_4$ from $^{13}CO_2$: Reproducibility Study

The production of $^{13}CH_4$ from $^{13}CO_2$ was evaluated at 34 days in 4 independent $^{13}CO_2$ reduction tests, conducted under reference conditions, with bacterial suspensions prepared from different *S. maltophilia* cultures. In all cases, a significant production of $^{13}CH_4$ was obtained, with $^{13}CH_4$ levels in the reactor headspace varying between 1 to 3% v/v.

3. Effect of Various Parameters on the Performance in Reduction of $^{13}CO_2$

Various parameters that can potentially influence the performance of the $CO_2$ reduction reaction are studied. To this end, tests are conducted under modified reaction conditions, in comparison with reference conditions. A test under reference conditions is always carried out simultaneously with the study of the influence of a parameter to determine the impact of the modified parameter.

a. Effect of Biomass Concentration

The initial mass concentration of the bacterial suspension used for the $^{13}CO_2$ reduction tests is set at 3.1±0.2 $g_{dry\ cells}$/L. Indeed, under the culture conditions used, this concentration is currently the highest possible one making it possible to launch different closed reactors and different series of closed reactors. In the end, the volumes and concentrations of bacteria produced can be increased. A lower concentration (1.6±0.1 $g_{dry\ cells}$/L) is tested to verify that the amount of $^{13}$C-formate produced is correlated with the amount of cells; the other reaction parameters remain unchanged. The kinetics are monitored over 25 days.

Table 2 summarizes the results obtained.

TABLE 2

Initial [X$_0$] and final [X$_f$] biomass mass concentrations (in $g_{dry\ cells}$/L), biomass loss Δ[X] at the end of the reaction (in %) and final accumulated $^{13}$C-formate concentrations derived from $^{13}CO_2$ reduction (in mmol/L and mg/L).

| [X$_0$] ($g_{dry\ cells}$/L) | [X$_f$] ($g_{dry\ cells}$/L) | Δ[X] (%) | [$^{13}$C-formate] (mmol/L) | [$^{13}$C-formate] (mg/L) |
|---|---|---|---|---|
| 3.1 | 1.1 | 65 | 0.65 | 29.3 |
| 1.6 | 0.7 | 56 | 0.03 | 1.4 |

Table 2 shows that the concentration of $^{13}$C-formate is nearly 20 times higher when the initial concentration of bacteria is doubled. Contrary to what could be expected, the final accumulated concentration of $^{13}$C-formate is therefore not correlated to the amounts of cells initially introduced. On the other hand, it is interesting to note that doubling the initial amount of bacteria also doubles the final amount of lysed cells (Table 2, difference between [X$_0$] and [X$_f$]). It is therefore possible that the compounds released into the reaction medium by cell lysis could be used by the surviving cells to produce a higher amount of intracellular $CO_2$-reducing enzyme, which would therefore lead to an increase in $^{13}$C-formate production.

In conclusion, the availability of intracellular compounds in the reaction medium seems to be a limiting factor for $CO_2$ reduction performance when the initial bacterial concentration is too low (1.6 $g_{dry\ cells}$/L).

b. Influence of the Nature of the Gas Mixture

Tests with different gas mixtures are carried out to study the influence of the presence of oxygen ($O_2$) and nitrogen ($N_2$) on the $CO_2$ reduction reaction. The concentration of $^{13}$C-formate is monitored.

Different initial gas mixtures containing $^{13}CO_2$ were tested: (i) the reference mixture composed of $^{13}CO_2$:atmospheric air (3:7 v/v), (ii) a $^{13}CO_2$:$N_2$ mixture (3:7 v/v) to study the influence of oxygen and (iii) pure $^{13}CO_2$ to study the effect of nitrogen. These tests were all repeated twice.

The results show that the absence of oxygen and the presence of nitrogen accelerate the appearance of $^{13}$C-formate in the medium. Indeed, the production of $^{13}$C-formate occurs on average 14±2 days earlier under the $^{13}CO_2$:$N_2$ (3:7 v/v) mixture, compared with the $^{13}CO_2$:atmospheric air mixture (3:7 v/v) and with pure $^{13}CO_2$. On the other hand, whatever the gas ceiling used, the maximum concentration of $^{13}$C-formate accumulated in the medium over a reaction time of 31 days remains of the same order of magnitude (around 0.1 mmol/L). Oxygen is reported to be a potential inhibitor of nitrogenase and FDH activities because it can act as an electron acceptor and lead to the formation of reactive oxygen species (J. Gallon, Trends in Biochemical Sciences, 1981, 6: p. 19-23) but it can also affect the synthesis of nitrogenase (Q. Liu et al., Nature communications, 2015, 6: p. 5933). The decrease in performance observed in the presence of $O_2$ is therefore unsurprising.

In conclusion, using a $^{13}CO_2:N_2$ mixture is favorable to the reaction kinetics of $^{13}CO_2$ reduction.

c. Influence of the Composition of the Reaction Medium

New $^{13}CO_2$ reduction tests are carried out with an ammonium ion enriched reaction medium (AERM). The AERM contains 2 mmol/L KCl, 28 mmol/L $NH_4Cl$, 30 mmol/L $NaHCO_3$ and 5 mmol/L $NaH_2PO_4$. The $^3C$-formate and ammonium ion ($NH_4^+$) concentrations are monitored throughout the reaction (FIG. 3).

Figure 3:
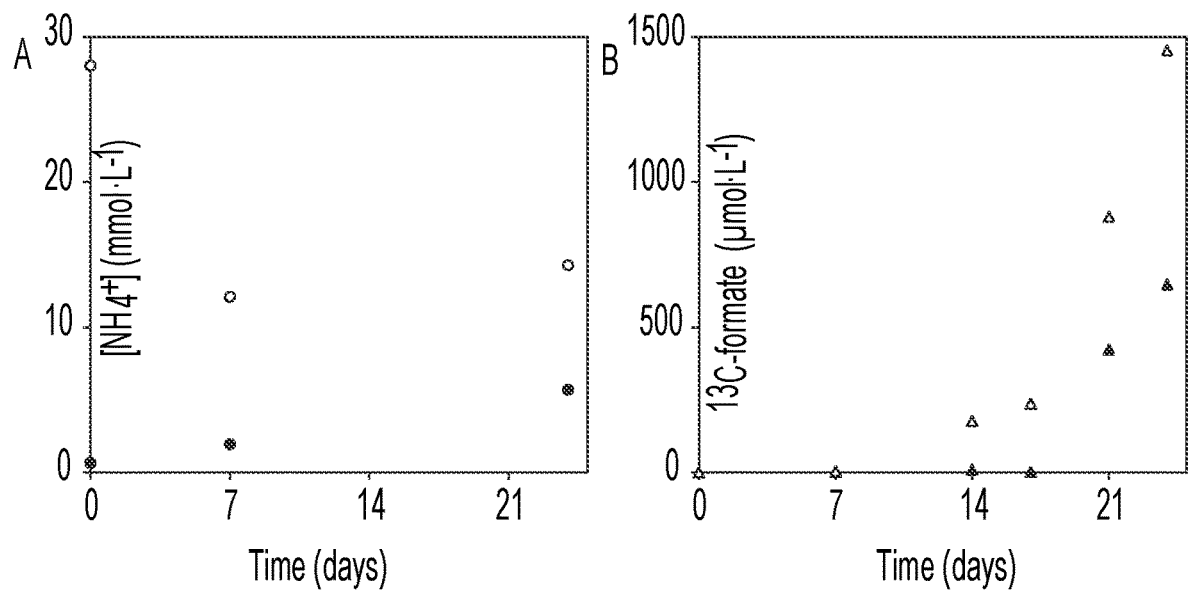
FIG. 3: $^{13}CO_2$ reduction tests in a closed reactor with a suspension of S. maltophilia prepared in an ammonium enriched reaction medium (AERM); the other reaction parameters being unchanged compared with the reference conditions. A $^{13}CO_2$ reduction test is also carried out simultaneously at reference conditions. (A) Change in the ammonium ion ($NH_4^+$) concentration: in the AERM (○) and in the reference reaction medium (●). (B) Change in the $^{13}$C-formate ($H^{13}COO^-$) concentration: in the AERM (△) and in the reference reaction medium (▲).

When ammonium ions are initially present in large amounts, almost half of the initial amount is consumed over the first 8 days, then the concentration seems to stabilize (FIG. 3.A). Under reference conditions, ammonium ions appear in suspension (FIG. 3.A). This appearance of ammonium ions can be linked to two productions: the reduction of $N_2$ by nitrogenase and the deamination of proteins released into the medium after cell lysis. Moreover, these $NH_4^+$ ions are not oxidized to nitrates or nitrites, which implies that these $NH_4^+$ ions can serve as a source of assimilable nitrogen for enzyme synthesis by surviving bacteria.

Concerning $^{13}C$-formate production, it is almost 2.5 times higher at 24 days (or a concentration of 1.45 mmol/L, i.e. about 65 mg/L) and occurs about 7 days earlier (FIG. 3.B) when the reaction medium is enriched with ammonium. This could be explained in particular by the fact that that the excess presence of a nitrogen source available to the bacterium (i.e. $NH_4^+$ ions) at the beginning of the reaction may have helped the bacterium to overexpress its $CO_2$-reducing enzyme system.

It is therefore also possible to make upstream adjustments of the culture conditions of the bacterium *S. maltophilia* and/or genetic modifications of the bacterium to overexpress the quantity of its $CO_2$-reducing enzymatic system and benefit from a higher intrinsic specific $CO_2$ reduction activity.

d. Study of the Reversibility of the $CO_2$ Reduction Reaction

This study showed that the bacterium *S. maltophilia* is capable of reducing $CO_2$ to formate. Up to now, the maximum accumulated formate concentration is about 1.5 mmol/L (i.e. 67.5 mg/L). In order to study the reversibility of the reaction of this catalytic system, i.e. its ability to oxidize formate to $CO_2$, a sodium $^{13}C$-formate concentration of 1.5 mmol/L is introduced into a suspension of *S. maltophilia* prepared as for a $CO_2$ reduction test (section A] 3). This suspension is then introduced into an NMR tube and analyzed by NMR (section A] 6). If the reduction equilibrium of $^{13}CO_2$ is reversible, then oxidation of $^{13}C$-formate ($H^{13}COO^-$) to $^{13}CO_2$ should be able to occur because $^{13}CO_2$ is initially a minority:

$H^{13}COO^- \leftrightarrow {}^{13}CO_2$ (Equation 6)

Figure 4:
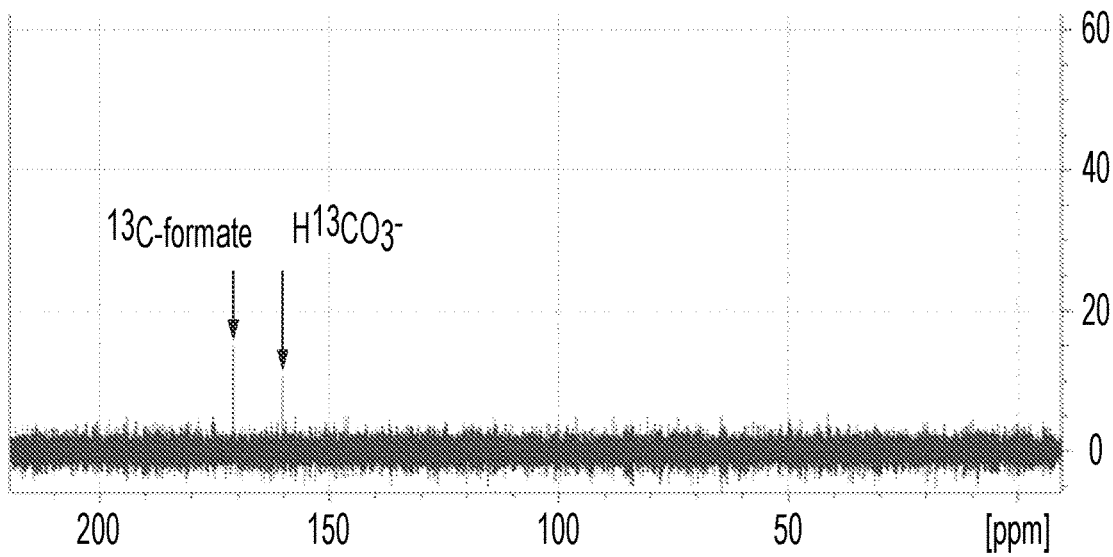
FIG. 4: NMR spectrum of a suspension of S. maltophilia initially enriched with 1.5 mM $^{13}$C-formate ($H^{13}COO^-$).

The NMR spectrum obtained after 4 h is shown in FIG. 4.

Only two peaks are visible, corresponding respectively to the $^{13}C$-formate ($\delta$=171.0 ppm) and $^{13}C$-hydrogen carbonate ($\delta$=160.2 ppm) ions. This result confirms that when the $^{13}C$-formate is predominant over $^{13}CO_2$, then the $^{13}C$-formate can be oxidized to $^{13}CO_2$, which solubilizes as hydrogen carbonate ($H^{13}CO_3^-$). Indeed, in the case of this test, the pH of the reaction medium (7.0±0.1) is higher than the pKa of the $CO_2,H_2O/HCO_3^-$ pair (6.4) because the medium is not buffered by the presence of $^{13}CO_2$. As was expected, the reaction catalyzed by the bacterium *S. malto-philia* thus seems to be regulated by the concentration of the most abundant substrate ($CO_2$ in the direction of reduction and formate in the opposite direction). Moreover, it is interesting to note that the presence of these two NMR peaks only, and thus the absence of other peaks, confirms that the formate produced under these reaction conditions is not used by the bacterium to form biomass or enzymes (section B] I.1). Continuous removal of formate is therefore a possible option to promote the $CO_2$ reduction reaction.

e. Influence of the Addition of PHB to the Reaction Medium

The enzymatic reduction of $CO_2$ requires a source of protons and electrons. Ammonium ions ($NH_4^+$) not being oxidized to nitrate or nitrite ions, it is therefore unlikely that they serve as electron and proton donors for the $CO_2$ reduction reaction. The source of protons and electrons is most likely accumulated in the cell during the culture phase of the bacteria as an energy reserve. At present, two types of molecules have been identified as being able to play this role: poly-3-hydroxybutyrate (PHB) which is a natural polymer and lipids. As far as PHB is concerned, bacterial cells are indeed able to depolymerize PHB to its monomer (3-hydroxybutyrate) and to oxidize this monomer to acetoacetate in order to recover electrons and protons but also a source of carbon (S. Obruca et al., PLoS One, 2016, 11(6): e0157778).

To verify the role of the PHB, it is initially added to the bacterial suspension and the $CO_2$ reduction reaction is then carried out under the reference conditions (described in section B] 1.2). However, PHB is a high molecular weight polymer and insoluble in water, which makes impossible its transport and its assimilation in the cell in its polymerized form. However, the bacterium *S. maltophilia* is capable of excreting depolymerases that can depolymerize PHB to its bacterially assimilable 3-hydroxybutyrate monomer (S. Wani et al., 3 Biotech, 2016, 6(2): p. 179-184; B. Tiwari et al., Bioresource technology, 2016, 216: p. 1102-1105).

To determine the amount of PHB to be added, the intracellular PHB contents of the bacterial suspensions used for the tests is first measured by the method detailed in section A] 6. A mean intracellular PHB mass content of 1.0±0.1% w/w is obtained, corresponding to a PHB concentration of 30±2 mg/L, which is rather common for *S. maltophilia* species (B. Iqbal et al., Annual Research & Review in Biology, 2016, 9(5): p. 1). A 10-fold higher concentration (300 mg/L, i.e. 0.3 g/L) is then used for testing to avoid PHB limitation.

Two independent series of closed reactors are prepared, using two different bacterial cultures. For each test, kinetics are conducted in parallel under the reference conditions (i.e. without addition of PHB). In all the tests, the gaseous atmosphere of the reactors is thus initially composed of a $^{13}CO_2$:atmospheric air mixture (3:7 v/v). For the first series, monitoring is carried out over 20 days and up to 40 days for the second series. The $^{13}C$-formate concentrations as well as the intracellular PHB concentrations are measured during the kinetics.

Table 3 presents the results obtained initially then at 20, 30 and 35 days. It is important to point out that PHB measurements for kinetics in which PHB is added are not indicated because they are not reproducible, likely due to a lack of homogeneity in the samples taken from the reactors (indeed, PHB is not soluble in water).

TABLE 3

Concentrations of $^{13}$C-formate ([$^{13}$C-formate] in μmol/L) and intracellular PHB ([PHB$_{intra}$] in mg/L).

| | Time (days) | 0 | 20 | 30 | 35 |
|---|---|---|---|---|---|
| Series 1 Reference Without PHB addition | [$^{13}$C-formate] (μmol/L) | 0 | 103 | — | — |
| | [PHB$_{intra}$] (mg/L) | 31 | 13 | — | — |
| Series 1 With PHB addition | [$^{13}$C-formate] (μmol/L) | 0 | 298 | — | — |
| | [PHB$_{intra}$] (mg/L) | NM | NM | — | — |
| Series 2 Reference Without PHB addition | [$^{13}$C-formate] (μmol/L) | 0 | 46 | 7 | 7 |
| | [PHB$_{intra}$] (mg/L) | 28 | 13 | 12 | 13 |
| Series 2 With PHB addition | [$^{13}$C-formate] (μmol/L) | 0 | 4 | 249 | 660 |
| | [PHB$_{intra}$] (mg/L) | NM | NM | NM | NM |

NM means Not Measurable and (—) means Not Measured.

Concerning $^{13}$C-formate production, production is much higher when PHB is initially added to the reaction medium. Compared with the reference conditions (without PHB addition), the concentration of $^{13}$C-formate produced in the presence of PHB is indeed increased by a factor between 3 and 95 (Table 3, series 1 and 2 respectively). This result shows that the addition of PHB improves the performance of the CO$_2$ reduction reaction and suggests that it could be an electron and proton donor for this reaction.

A PHB limitation in the reference conditions could explain why the production of $^{13}$C-formate is improved when the medium is enriched in PHB. Indeed, under the reference conditions (without PHB addition), the intracellular PHB concentration decreases from 30±2 to 13±1 mg/L regardless of the kinetics and then remains constant (Table 3, series 1 and 2). For both series, it thus appears that about 20 mg/L of intracellular PHB is consumed by the cells during the reaction. Moreover, the PHB limitation is probably not the only parameter to impact the production of $^{13}$C-formate. Indeed, under the reference conditions and for the same amount of PHB consumed after 20 days of reaction, the $^{13}$C-formate concentration obtained at 20 days is almost twice as high for series 1 as for series 2 (Table 3). This can be explained by the fact that these series were made from two different cultures and that the physiological state of the bacteria was not the same. However, the physiological state can play a role on the intrinsic CO$_2$-reducing activity of the bacteria but also on its ability to adapt to its new CO$_2$ substrate.

In conclusion, the amount of intracellular PHB is a limiting factor for the CO$_2$ reduction reaction and for the production of $^{13}$C-formate. The PHB is thus likely a source of electrons and protons for the CO$_2$ reduction reaction.

4. Study of Synergistic Effects with Other Bacteria

The bacterium *S. maltophilia* was put in consortium with bacteria likely to use formate to study their possible synergies.

First, a consortium formed by the bacterium *S. maltophilia* and the methanotrophic bacterium *M. trichosporium* OB3b, obtained after culture on methane (according to the protocol described in section A] 1), was implemented under the CO$_2$ reduction reaction conditions detailed in section A] 4. NMR analysis of the reaction medium was conducted initially and after 8 days. The NMR spectra obtained are presented in FIG. 5.

Figure 5:
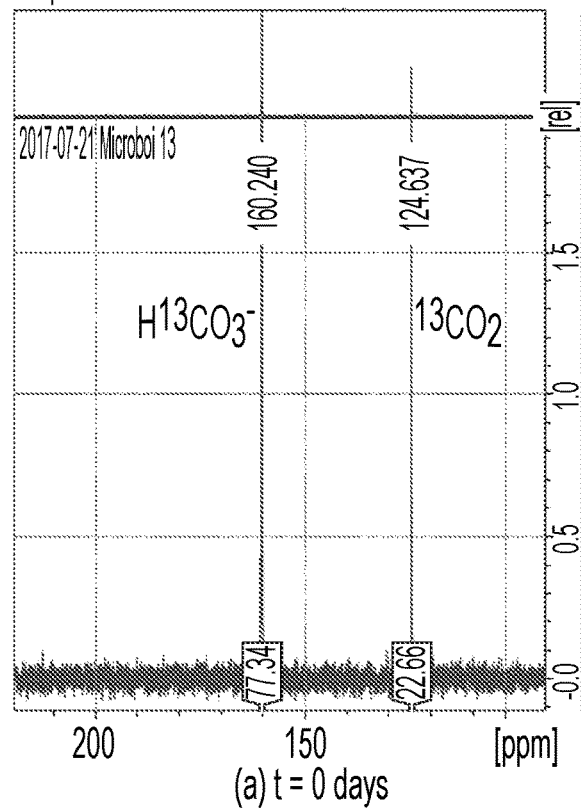
FIG. 5. NMR spectra of the reaction medium containing the S. maltophilia/M. trichosporium OB3b consortium obtained in the presence of $^{13}CO_2$ at (a) t=0 days, where the $^{13}CO_2$ and its basic form $H^{13}CO_3^-$ are present and (b) t=8 days showing the appearance of a $^{13}$C-formate peak.
Figure 5:
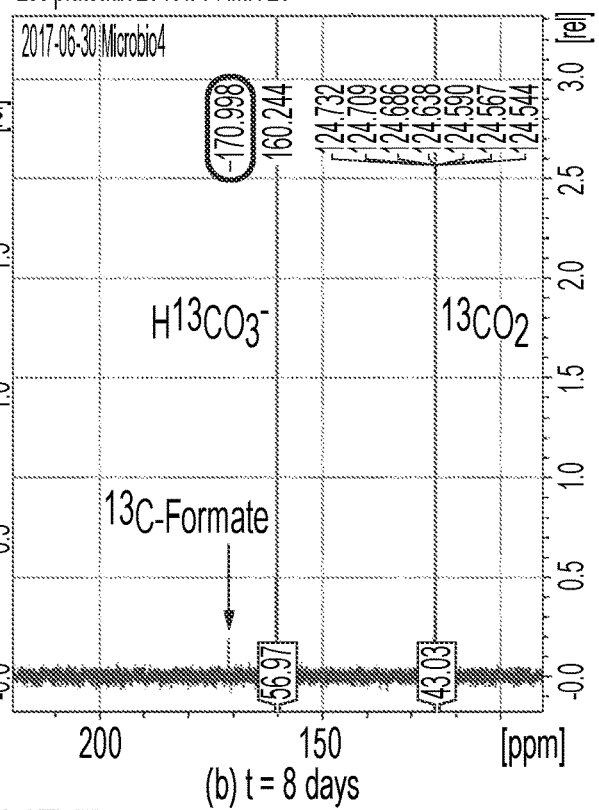

From the beginning (t=0 days) and throughout the reaction, the resonance peaks of the $^{13}$CO$_2$ (δ=124.6 ppm) and its ionic form H$^{13}$CO$_3^-$ (δ=160.2 ppm) are still visible (FIG. 5.*a*). After 8 days of kinetics, a new peak appears (δ=171.0 ppm, FIG. 5.*b*), corresponding to the fingerprint of the standard made with $^{13}$C-labeled formate. This demonstrates the production of $^{13}$C-formate under these conditions, at a concentration greater than or equal to the detection limit of labeled formate by NMR analysis, i.e. 6 mg·L$^{-1}$. NMR analysis of the supernatant revealed no labeled $^{13}$C-formate, meaning that the labeled formate produced is intracellular, as observed in kinetics with *S. maltophilia* alone.

No other labeled products were found in the NMR spectrum (FIG. 5.*b*). Tests conducted over 8 days with the methanotrophic bacterium *M. trichosporium* OB3b alone, whose purity was confirmed beforehand, showed that this bacterium does not catalyze CO$_2$ reduction. Furthermore, this bacterium is capable of forming spores that limit the interactions of the bacterium with its environment, which may explain why no synergy between *S. maltophilia* and *M. trichosporium* OB3b was observed.

This result therefore suggests that the presence of this methanotrophic bacterium in the reaction medium does not interfere with CO$_2$ reduction and formate production by *S. maltophilia*. For certain applications, co-culturing the *S. maltophilia* biocatalyst with the methanotrophic bacterium *M. trichosporium* OB3b can therefore be considered to guarantee an optimal carbon balance since methane, of renewable origin, would be the sole source of carbon necessary for the culture.

Second, a consortium formed by the bacterium *S. maltophilia* and the Gram-positive *bacillus* type bacterium *Microbacterium oxydans*, obtained after culture on LB medium (according to a protocol similar to that described in section A] 1), was implemented under the CO$_2$ reduction reaction conditions detailed in section A] 4. NMR analysis of the reaction medium was performed at 5, 8 and 12 days (FIG. 6).

Like the initial spectrum obtained with the *S. maltophilia/M. trichosporium* OB3b consortium, only the peaks of the substrates ($^{13}$CO$_2$ and H$^{13}$CO$_3^-$) are visible at t=0 days.

After 5 days of reaction, a formate peak appears (δ=170.9 ppm, FIG. 6.*a*), corresponding to a concentration greater than or equal to 6 mg·L$^{-1}$. Compared with kinetics performed in pure culture with *S. maltophilia*, the latency time appears reduced by at least two days (FIGS. 1 and 6). Furthermore, NMR analysis of the supernatant did not reveal the presence of labeled products, thus showing that the labeled formate is also produced intracellularly.

Figure 6:
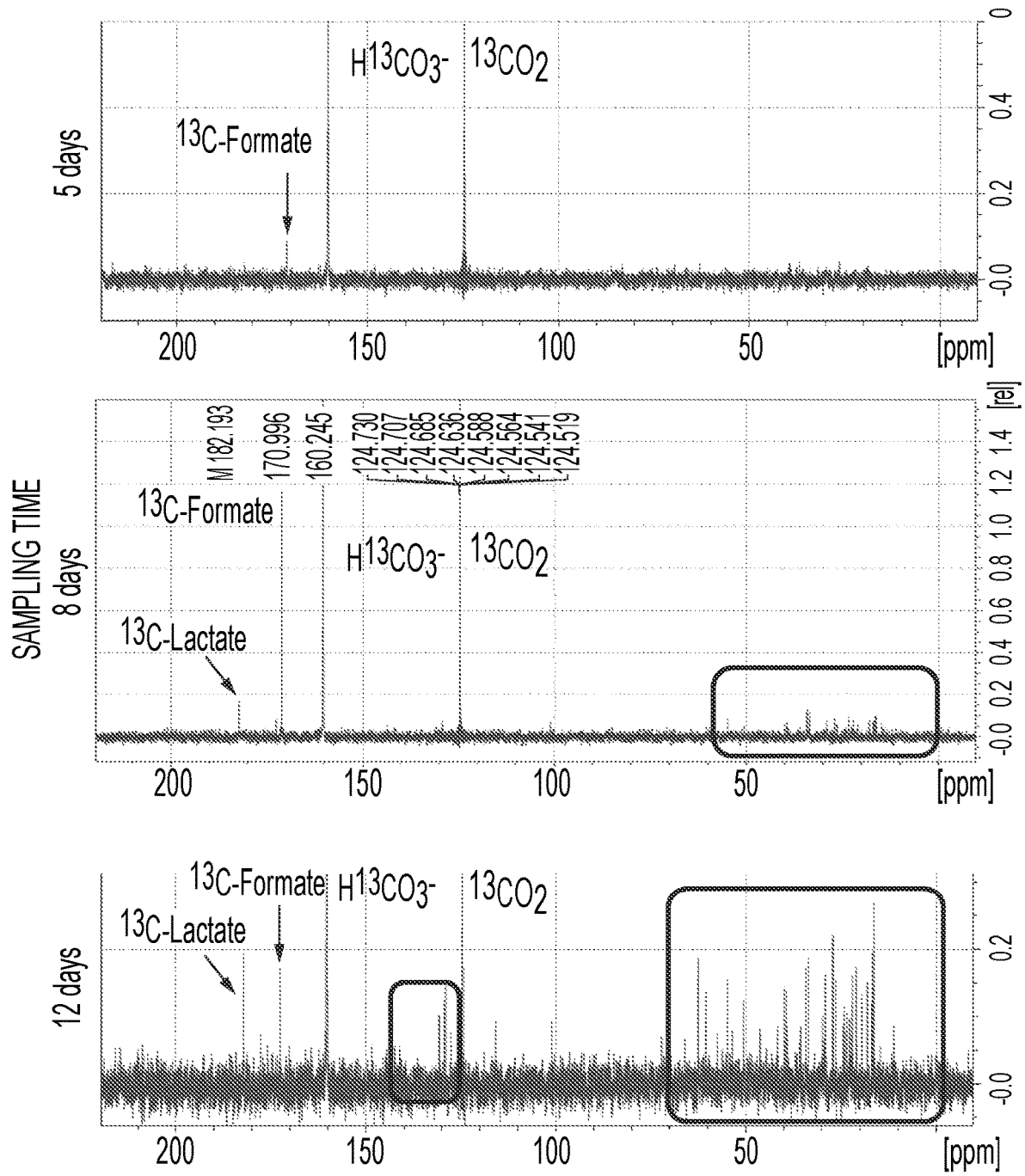
FIG. 6. NMR spectra of the reaction medium containing the S. maltophilia/M. oxidans consortium obtained in the presence of $^{13}CO_2$ at (a) t=5 days; (b) t=8 days and (c) t=12 days.

After 8 days of reaction, the amplitude of the formate peak increases significantly (by a factor of about 10), which means that the concentration of formate produced is higher than at 5 days (FIGS. 6.*a* and 6.*b*). In addition, new intracellular peaks labeled with $^{13}$C appear, including a peak (δ=182.2 ppm) that may correspond to the fingerprint of one of the three carbons contained in the lactate, as well as a forest of peaks in the area of chemical displacements comprised between 15-65 ppm (FIG. 6.b).

After 12 days of kinetics, the amplitude of the NMR peak relative to the formate decreases significantly (by a factor of about 10) compared with the peak obtained at 8 days (FIGS. 6.b and 6.c). The compound that seems to be lactate is still present, in proportions comparable to those obtained at 8 days. On the other hand, the peak forest visible in the chemical shift zone comprised between 15-65 ppm is more intense (FIGS. 6.b and 6.c) and new $^{13}$C-labeled compounds also appear in the chemical shift zone between 125-140 ppm (FIG. 6.c). This phenomenon is characteristic of a metabolic activity of the cells. As the three carbons of the lactate are not labeled, it is important to stress that this labeled lactate cannot therefore come from a direct reduction of $^{13}CO_2$. This production of labeled lactate can nevertheless result from the binding of $^{13}CO_2$ and/or $^{13}$C-formate to organic molecules already initially present in the cells, as well as labeled compounds related to new peaks ($\delta$=125-140 ppm).

A possible explanation for these observations is the establishment of a synergy between the two bacteria present. Indeed, S. maltophilia can reduce $CO_2$ to formate, then excrete the formate produced outside its cell so that M. oxydans can use it and form new compounds necessary for its subsistence such as lactate or other products whose fingerprints are comprised in the peak forests. Nevertheless, NMR analysis of the supernatant revealed only the signals from the $^{13}CO_2$ and $H^{13}CO_3^-$ substrates but not that of the $^{13}$C-formate. A probable hypothesis is that the M. oxydans bacterium captures and introduces the formate produced in its cells as soon as the formate has been excreted by the S. maltophilia bacterium, which would explain the significant decrease of the $^{13}$C-formate peak observed at 12 days (FIG. 6.c). The presence of M. oxydans bacteria would therefore boost the reduction of $CO_2$ by S. maltophilia and thus the production of $^{13}$C-formate; this may also explain the decrease in the latency phase for the production of $^{13}$C-formate. Such a synergy between S. maltophilia and M. oxydans is quite realistic under these reaction conditions (i.e. under pure $CO_2$) because M. oxydans is facultatively aerobic (P. Schumann et al., International Journal of Systematic and Evolutionary Microbiology, 1999, 49(1): p. 175-177); this is not the case for M. trichosporium OB3b which is strictly aerobic (N. Dorina et al., Applied biochemistry and microbiology, 2008, 44(2): p. 182-185).

II. $CO_2$ Reduction Test in a Semi-Closed Reactor, Assisted by Electrolysis

1. Electrochemical Device and its Principle

The polymer poly-3-hydroxybutyrate (PHB) is depolymerized to 3-hydroxybutyrate which is an identified electron and proton donor for the $CO_2$ reduction reaction (section B] I.3.e]). Nevertheless, the intracellular stock of PHB is finite. The idea is therefore to provide without limitation and continuously the electrons and protons required for the reaction by virtue of an inexpensive in situ electrolytic device, so that the performance of the $CO_2$ reduction reaction is improved and lasting over time. This electrochemical device therefore aims at replacing intracellular proton and electron donors. A semi-closed electrolysis-assisted reactor (or bioelectrolyzer) was thus implemented to intensify the $CO_2$ reduction reaction catalyzed by the bacterium S. maltophilia.

In this 3-electrode device (FIG. 7 and section A] 5), the role of the polarized cathode is to provide the electrons necessary for the reduction reaction of $CO_2$ to a compound whose average carbon oxidation number is lower than that of the carbon in the $CO_2$ molecule (this compound is denoted $CO_{2,reduced}$) whereas the oxidation of water at the anode both supplies the protons and closes the electric circuit; the reference electrode, in turn, maintains a constant polarization voltage ($V_{polarization}$) at the cathode. Conventionally, an Ag/AgCl reference electrode is used. A necessary condition for this device to work is that the S. maltophilia bacterium is electroactive in reduction, i.e. capable of exchanging electrons with the cathode. So far, the bacterium S. maltophilia is only known to exchange electrons in oxidation, i.e. with an anode (K. Venkidusamy and M. Megharaj, Frontiers in microbiology, 2016, 7: p. 509-518; H. Xue et al., Sensores and Actuators B: Chemical, 2017, 243: p. 303-310; J. Shen et al., Bioelectrochemistry, 2017, 114: p. 1-7).

First, the polarization voltage is chosen on a thermodynamic basis. The oxidation-reduction potential of the acetoacetate/3-hydroxybutyrate pair being −0.53 V vs Ag/AgCl at pH 6.4 (P. A. Loach, Handbook of Biochemistry and Molecular Biology, 1976, 1: p. 122), it is therefore necessary to initially impose a higher potential (by absolute value) than this potential (such as for example −0.7 V vs Ag/AgCl) so that the bacterium has an energetic interest in using the electrons of the electrode rather than those coming from the oxidation of 3-hydroxybutyrate. Nevertheless, if the stock of intracellular PHB, energy source and 3-hydroxybutyrate is depleted during the reaction by the general metabolism of the bacterium, this constraint on the potential will be lifted and a potential lower (by absolute value) than −0.53 V vs Ag/AgCl at pH 6.4 can be implemented. Furthermore, the selected potential is preferentially chosen lower than those of the oxidizer-reducer pairs $CO_2/CO_{2,reduced}$ involving $CO_2$ as oxidant so as to favor the reduction of $CO_2$ at the cathode; the choice of the polarization potential also makes it possible to favor the production of a reduction product $CO_{2,reduced}$ compared with other possible $CO_2$ reduction products (among methane and formate for example). In general, a potential greater than or equal to −0.8 V vs Ag/AgCl (for example −0.7 V vs Ag/AgCl) will (i) limit the reduction of the proton to hydrogen ($H_2$) and (ii) avoid the reduction of phosphates and magnesium ions present in the reaction medium. The minimum potentials below which proton and $CO_2$ reductions occur can be precisely determined by cyclic voltammetry, under the reaction conditions, to take into account both thermodynamic and kinetic phenomena (overvoltages); overvoltages depending in particular on the material chosen for the cathode.

According to the literature, the nature of the material can also have a significant impact on the establishment of electron transfer between the bacteria and the working electrode (M. Rosenbaum et al., Bioresource Technology, 2010, 102(1): p. 324-333). The chemical composition and the surface structure can indeed induce different electrochemical responses. Among the numerous electrode materials available, graphite is porous and has a surface roughness. Graphite is therefore likely to promote contact between the bacteria and the electrode, which could promote electronic conduction (M. Rosenbaum et al., Bioresource Technology, 2010, 102(1): p. 324-333). Graphite is therefore chosen as the cathode material for the tests presented. In addition, a platinum anode is chosen for these tests in order to reduce the anode overvoltages and not to limit the cathodic phenomena. Other anode materials can also be considered, such as steel. An anode surface larger than the cathode surface is also preferred so as not to limit the reduction reactions at the cathode.

Furthermore, a continuous bubbling of pure $CO_2$ is also implemented to saturate the suspension with $CO_2$ and deoxygenate the solution so as to (1) avoid competition with the aerobic metabolic pathway (where $O_2$ would become an electron acceptor instead of $CO_2$) and (2) preserve the catalytic activity of the $CO_2$-reducing enzyme (indeed, oxygen seems to have an inhibitory effect on this enzyme, section B] I.3.b). In order to guarantee an optimal gas-liquid mass transfer, the $CO_2$ supply is achieved by a porous gas distributor and a volume of liquid (allowing a high volume of gas per volume of liquid per minute, or VVM) is used. A high cathode surface/liquid volume ratio is also desirable to concentrate the product formed by $CO_2$ reduction at the cathode; a cathode surface/liquid volume ratio of around 10 $m^2/m^3$ is desirable.

2. A First Example of a Bioelectrolyzer Fed by Pure $CO_2$

Figure 8:
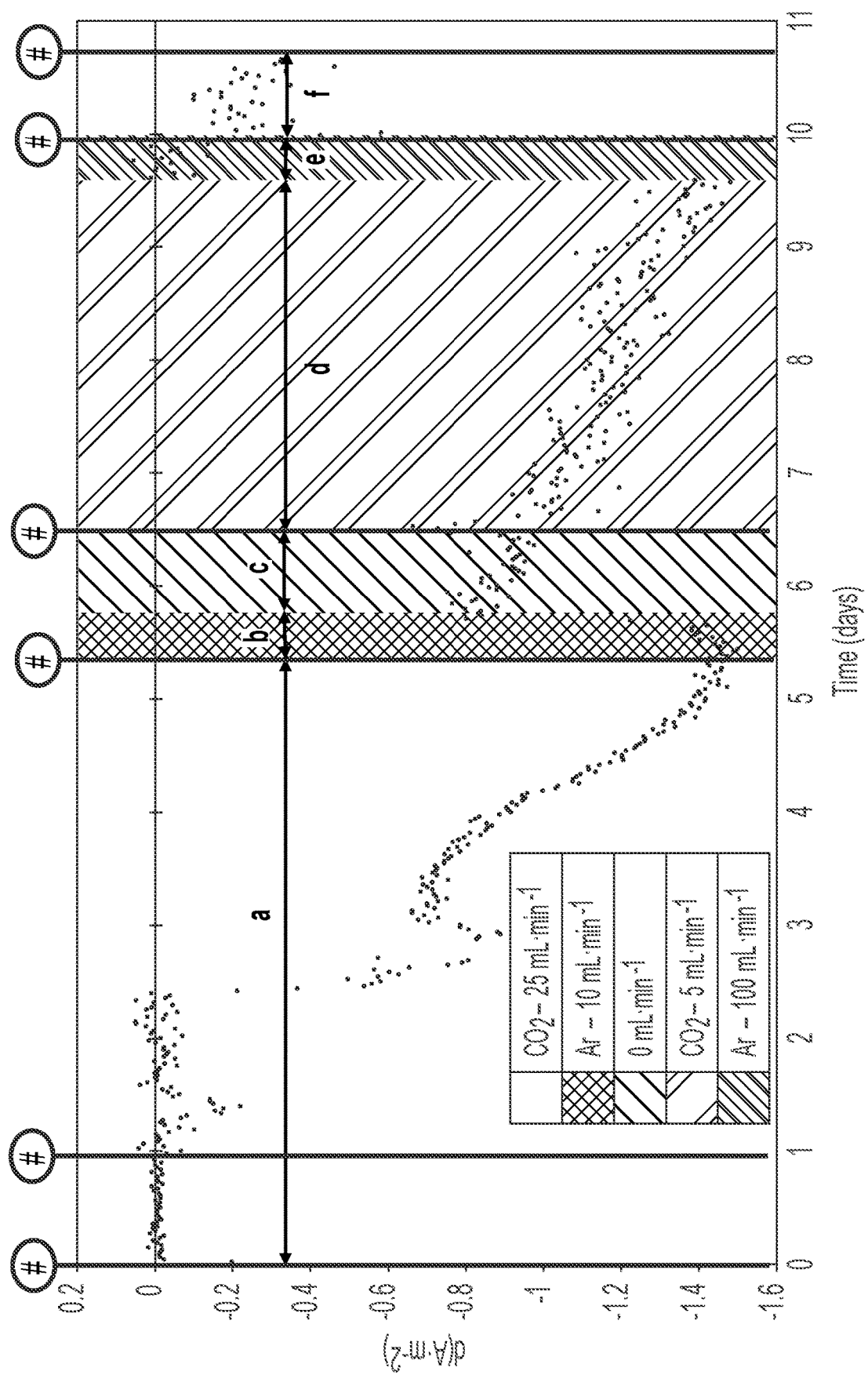
FIG. 8. Change in the cathode current density measured over time in a bioelectrolyzer inoculated with *Stenotrophomonas maltophilia*, according to an embodiment of the process of the invention. The polarization voltage is set at –0.7 V vs Ag/AgCl. Six phases are distinguished, corresponding to the different operating conditions used: (a) $CO_2$ bubbling (25 mL·min$^{-1}$); (b) argon bubbling, noted Ar (10 mL·min$^{-1}$); (c) argon bubbling stopped; (d) $CO_2$ bubbling (5 mL·min$^{-1}$); (e) argon bubbling (100 mL·min$^{-1}$) and (f) $CO_2$ bubbling (25 mL·min$^{-1}$). The symbol (#) indicates the polarization interruptions for the acquisition of cyclic voltammetries carried out at 10 mV·s$^{-1}$.

FIG. 8 shows the change in the measured current over time for the first bioelectrolyzer implemented with the bacterium S. maltophilia for $CO_2$ reduction. This current is expressed in current density (i.e. in $A/m^2$); the current density corresponds to the measured current (in A) relative to the projected cathode area (in $m^2$). The test is conducted with a polarization voltage of −0.7 V vs Ag/AgCl.

The initial zero current (0.0±0.01 $A/m^2$) corresponds to the baseline (FIG. 8.a), which is confirmed by the cyclic voltammetry performed at the beginning of the kinetics (data not shown). This thus shows that initially, no element present in the bacterial suspension oxidizes or reduces.

Then, a small reduction current is observed (to −0.2 A/m2 at 1.2 days). However, this current returns to the baseline before a significant reduction current appears from the second day forward (FIG. 8.a); the profile of this current follows a pattern comparable to that of microbial growth kinetics (FIG. 8.a). There is however no visible microbial growth in the suspension because the optical density ($OD_{600}$) of the bacterial suspension initially measured is 5.6 whereas it is 2.2 at 5.7 days (i.e. 136 h). Nevertheless, this does not exclude the growth of a biofilm on the cathode surface; the bacterium S. maltophilia is indeed capable of rapidly forming biofilms on different types of surfaces (O. Madhi et al., Current protocols in microbiology, 2014, 32: Unit-6F.1.1-6F.1.6).

In order to experimentally verify the dependence of this reduction current on $CO_2$, bubbling of an inert noble gas (argon) was carried out with the aim of driving out all or part of the dissolved $CO_2$. A first argon bubbling at a flow rate of 10 mL·min$^{-1}$ is carried out for 3 h and resulted in a near instantaneous reduction of the reduction current by a factor of about 2, from −1.4 to −0.8 $A/m^2$ (FIGS. 8.a and 8.b). Then, all gas flow is cut off and the reduction current remains near constant at around −0.8 $A/m^2$ (FIG. 8.c). The constancy of the reduction current can be explained by the presence of residual $CO_2$ in the bacterial suspension; indeed, $CO_2$ is very soluble in water and the imposed argon flow was probably too low to drive out all the dissolved $CO_2$.

When a low $CO_2$ flow rate is reapplied (5 mL·min$^{-1}$), then the reduction current increases again, until it returns to its initial stable value, i.e. −1.4 $A/m^2$ FIGS. 8.a and 8.d). Then, the application of a high argon flow (100 mL·min$^{-1}$) for 3 h results in the disappearance of any reduction current since the current rises to 0.0 $A/m^2$ (FIG. 8.e). These conditions are thus sufficient to drive out all the dissolved $CO_2$ in the suspension and confirm that neither proton nor phosphate reduction occurs at this polarization potential (−0.7 V vs Ag/AgCl). Finally, the current re-increases when a $CO_2$ flow is realized again (at 25 mL·min$^{-1}$) and reaches a significant value of −0.3 $A/m^2$ (FIG. 8.f). All these elements show that the reduction current is well related to $CO_2$ availability in the reaction medium and that $CO_2$ is the element that is reduced at the cathode.

The reaction that occurs at the cathode is therefore:

$$CO_2 + H^+ + 2e^- \rightarrow HCOO^- \quad \text{(Equation 7)}$$

This reduction reaction results from the enzymatic activity of the cell which no longer requires intracellular electron and proton donors.

Cyclic voltammetries (CVs) are also performed during the experiment. In particular, a CV performed at 5.7 days confirms the adequacy of the measured current with the imposed polarization potential (data not shown). This voltammetry also shows a diffusion step for the reduction current ranging from −0.2 V to −0.8 V vs Ag/AgCl, which suggests that a lower polarization voltage per absolute value (for example −0.2 V vs Ag/AgCl) may be sufficient to obtain the same reduction current.

In conclusion, this experiment demonstrates the ability of this bioelectrolytic device to replace the intracellular electron and proton donors necessary for the reduction of $CO_2$ catalyzed by the bacterium S. maltophilia.

3. Reproducibility Study

In addition to the test presented above, four other independent bioelectrolyzer tests according to the mode described by the Invention confirmed, by alternating pure $CO_2$/argon/pure $CO_2$ bubbling, that the $CO_2$ is indeed reduced at the cathode and that it generates a significant $CO_2$-dependent reduction current (data not shown). During these tests, two polarization potentials were tested: −0.7 V and −0.8 V vs Ag/AgCl and $CO_2$ reduction current densities comprised between −0.5 and −1.5 $A/m^2$ were obtained.

Furthermore, these tests validated the fact that the $CO_2$ reduction current stabilizes after a few days of $CO_2$ bubbling and that after argon bubbling, $CO_2$ bubbling allows the current to return to its stable value (reached before argon bubbling). This demonstrates the robustness of this bioelectrolysis system.

4. An Example of a Bioelectrolyzer Fed by a $CO_2/CH_4$ Mixture

An additional bioelectrolyzer test demonstrated that the presence of methane ($CH_4$) in the gas mixture that contains $CO_2$ and that feeds the bioelectrolyzer has no influence on the $CO_2$-reducing activity of the bacterium S. maltophilia at the cathode (data not shown). Indeed, a $CO_2/CH_4$ bubbling (1:1 or 1:2 v/v) maintains a reduction current equivalent to that obtained under pure $CO_2$ under the same conditions. This result is particularly attractive in the treatment of biogas, containing high levels of $CH_4$ and $CO_2$.

GC-TCD analysis of the bioelectrolyzer inlet and outlet gases measured an experimental volume flow of reduced $CO_2$ of 1.3 mL $CO_2$/min for a 60 mL reactor volume (thus equivalent to a flow of 1.9 $m^3$ $CO_2$/d for a 60 L reactor volume). This flow is nearly 60 times higher than the theoretical volume flow of reduced $CO_2$ ($F_{CO2,vol}$) calculable on the basis of the $CO_2$ reduction current obtained (by Faraday's law). This means that it is not only the bacteria adhering to the cathode that participate in the $CO_2$ reduction, but also the planktonic bacteria (suspended in the bioelectrolyzer liquid). A possible fixation of this $CO_2$ by planktonic bacteria cannot be excluded.

Finally, it is important to note that the experimental volume flow of reduced $CO_2$ in the bioelectrolyzer (i.e. 1.3 mL $CO_2$/min) is 130 times higher than that obtained in a closed reactor (i.e. 0.6 mL $CO_2$/d=0.01 mL $CO_2$/min for an initial bacterial concentration of 2 $g_{dry\ cells}$/L, Table 1). This significant increase in the bioelectrolyzer can be justified by (1) an improved $CO_2$ mass transfer thanks to the gas supply within the suspension and (2) an electrochemical assistance that provides the bacteria with an inexhaustible source of electrons and protons.

The invention claimed is:

1. A process for the recovery of $CO_2$ by biological reduction comprising a step of bringing a liquid phase containing the bacterium *Stenotrophomonas maltophilia* into contact with a $CO_2$-containing gas phase under conditions allowing the reduction of $CO_2$.

2. The process for the recovery of $CO_2$ by biological reduction according to claim 1, wherein the step of bringing the liquid phase and the $CO_2$-containing gas phase into contact is carried out in a semi-closed or continuous reactor, wherein the $CO_2$-containing gas phase is supplied continuously into the reactor.

3. The process for the recovery of $CO_2$ by biological reduction according to claim 1, wherein formate and/or methane ($CH_4$) is produced by $CO_2$ reduction.

4. The process for the recovery of $CO_2$ by biological reduction according to claim 1, comprising a preliminary phase of co-culture of *Stenotrophomonas maltophilia* with at least one methanotrophic bacterium before the step of bringing the liquid phase into contact with the gas phase.

5. The process for the recovery of $CO_2$ by biological reduction according to claim 1, wherein the liquid phase also contains at least one microorganism capable of using the formate to produce organic compounds of interest.

6. The process for the recovery of $CO_2$ by biological reduction according to claim 1, wherein the gas phase is a biogas or $CO_2$-rich industrial and/or agricultural fumes.

7. The process for the recovery of $CO_2$ by biological reduction according to claim 1, wherein the gas phase comprises at least 30% by volume of $CO_2$ relative to the total volume of the gas phase.

8. The process for the recovery of $CO_2$ by biological reduction according to claim 1, wherein the gas phase comprises between 30% and 100% by volume of $CO_2$ with respect to the total volume of the gas phase.

9. The process for the recovery of $CO_2$ by biological reduction according to claim 1, wherein the liquid phase comprises at least 3 $g_{dry\ cells}/L$ of *Stenotrophomonas maltophilia*.

10. The process for the recovery of $CO_2$ by biological reduction according to claim 1, wherein ammonium and/or ammonia is added in the liquid phase and/or ammonia is added in the gas phase.

11. The process for the recovery of $CO_2$ by biological reduction according to claim 1, wherein PHB is added in the liquid phase.

12. The process for the recovery of $CO_2$ by biological reduction according to claim 1, wherein formate is produced, said process comprising an additional step of recovering the formate produced in the form of formate and/or formic acid and/or organic compounds of interest derived from the use of the formate by a microorganism capable of using formate to produce organic compounds of interest.

13. The process for the recovery of $CO_2$ by biological reduction according to claim 1, wherein the step of bringing the liquid phase into contact with $CO_2$ is carried out in a closed or semi-closed or continuous reactor.

14. The process for the recovery of $CO_2$ by biological reduction according to claim 13, wherein the $CO_2$-containing gas phase is injected into the center of the reactor.

15. The process for the recovery of $CO_2$ by biological reduction according to claim 13, wherein the air present in a reactor headspace is removed, and the $CO_2$-containing gas phase is injected into said reactor headspace, so as to place the $CO_2$ reduction reaction under an atmosphere consisting solely of said gas phase.

16. The process for the recovery of $CO_2$ by biological reduction according to claim 13, wherein the step of bringing the liquid phase and the $CO_2$-containing gas phase into contact is carried out in the presence of an intra or extracellular electron and proton donor.

17. The process for the recovery of $CO_2$ by biological reduction according to claim 13, wherein the reactor contains an electrochemical assistance.

18. The process for the recovery of $CO_2$ by biological reduction according to claim 13, wherein the $CO_2$-containing gas phase is injected into the center of the reactor by a gas distributor.

19. A process for the treatment of a biogas or of $CO_2$-rich industrial fumes and/or $CO_2$-rich agricultural fumes comprising a step of reduction of the $CO_2$ by biological reduction comprising a step according to which said biogas and/or fumes are brought into contact with a liquid phase containing the bacterium *Stenotrophomonas maltophilia* under conditions allowing the reduction of the $CO_2$.

20. A process for the production of formate from $CO_2$, comprising a step in which a $CO_2$-containing gas phase is brought into contact with a liquid phase containing the bacterium *Stenotrophomonas maltophilia* under conditions allowing reduction of the $CO_2$ to formate or methane.

* * * * *